United States Patent
Ganapathy-Kanniappan et al.

(10) Patent No.: US 11,241,402 B2
(45) Date of Patent: Feb. 8, 2022

(54) METHODS OF TREATING LIVER FIBROSIS BY ADMINISTERING 3-BROMOPYRUVATE

(71) Applicant: The Johns Hopkins University, Baltimore, MD (US)

(72) Inventors: Shanmugasundaram Ganapathy-Kanniappan, Baltimore, MD (US); Surojit Sur, Gaithersburg, MD (US); Bert Vogelstein, Baltimore, MD (US); Kenneth W. Kinzler, Baltimore, MD (US); Jean-Francois Geschwind, Westport, CT (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/931,913

(22) Filed: Jul. 17, 2020

(65) Prior Publication Data
US 2021/0000772 A1    Jan. 7, 2021

Related U.S. Application Data

(62) Division of application No. 15/773,898, filed as application No. PCT/US2016/060537 on Nov. 4, 2016, now Pat. No. 10,751,306.

(60) Provisional application No. 62/252,116, filed on Nov. 6, 2015.

(51) Int. Cl.
*A61K 31/19* (2006.01)
*A61P 1/16* (2006.01)

(52) U.S. Cl.
CPC ............. *A61K 31/19* (2013.01); *A61P 1/16* (2018.01)

(58) Field of Classification Search
CPC .................................. A61K 31/19; A61P 1/16
USPC .......................................................... 514/557
See application file for complete search history.

(56) References Cited

U.S. PATENT DOCUMENTS

2010/0221220 A1 *  9/2010  Ko .................. A61K 31/56
424/85.7

OTHER PUBLICATIONS

Kang et al Hepatology, 2011, 54(2), 707-713 (Year: 2011).*

* cited by examiner

*Primary Examiner* — Yevgeny Valenrod
(74) *Attorney, Agent, or Firm* — Foley Hoag LLP

(57) ABSTRACT

Methods for treating or preventing liver fibrosis in a subject by administering to the subject a therapeutically effective amount of 3-bromopyruvate (3-BrPA) are provided. In addition, methods for promoting the reversal of an activated hepatic stellate cell (HSC) to an inactivated HSC by contacting the activated HSC with at least one 3-bromopyruvate (3-BrPA) molecule are also provided.

4 Claims, 15 Drawing Sheets

Specification includes a Sequence Listing.

A

B

C

A

B

C

D

D

B

C

D

E

F

G

H

I

J

K

L

M

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
tccaagtttg ctgacctctc                                               20

<210> SEQ ID NO 2
<211> LENGTH: 20
<212> TYPE: DNA
<213> ORGANISM: Artificial Sequence
<220> FEATURE:
<223> OTHER INFORMATION: synthetic primer

<400> SEQUENCE: 2
tcaacggcaa agttctcttc                                               20

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
tggatggacc ttatgttgct                                               20

<210> SEQ ID NO 4
<211> LENGTH: 20
<212> TYPE: DNA
<213> ORGANISM: Artificial Sequence
<220> FEATURE:
<223> OTHER INFORMATION: synthetic primer

<400> SEQUENCE: 4
aacacctgtc ttgggatcaa                                               20

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
```

```
accccacatc cttctcactg                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
tacaaaaacc cacgcagaca                                              20

<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
gcagtccaaa atcgagaaga                                              20

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
accagcttgc tcagaatcac                                              20
```

METHODS OF TREATING LIVER FIBROSIS BY ADMINISTERING 3-BROMOPYRUVATE

CROSS-REFERENCE TO RELATED APPLICATIONS

This application is a divisional application of U.S. Ser. application Ser. No. 15/773,898, filed on May 4, 2018, which is a national stage filing under 35 U.S.C. § 371 of PCT/US16/060537, filed on Nov. 4, 2016, which claims the benefit of priority to U.S. Provisional Application No. 62/252,116, filed Nov. 6 2015, the entire contents of each of which are hereby incorporated herein in their entirety by this reference.

SEQUENCE LISTING

The instant application contains a Sequence Listing which has been filed electronically in ASCII format and is hereby incorporated by reference in its entirety. Said ASCII copy, created on Sep. 14, 2020, is named as JHV-11502_ST25.txt and is 1897 bytes in size.

BACKGROUND OF THE INVENTION

Hepatocellular carcinoma (HCC) is the fifth most common cause of cancer worldwide and the third most common cause of cancer related mortality (Jemal et al., 2011). Surgical resection and liver transplantation have long been the only two treatment options that offer the possibility of a cure for patients with HCC (El-Serag and Rudolph, 2007; El-Serag, 2011; Llovet and Bruix, 2008). Other locoregional therapies, however, including percutaneous ethanol injection and thermal ablation, now appear to be rivaling surgical resection in terms of efficacy (Lencioni, 2010; Liapi and Geschwind, 2010, Ann. Surg. Oncol.; Liapi and Geschwind, 2010, J. Hepatobiliary Pancreat. Sci.).

Unfortunately, only 10-15% of the patients with HCC are eligible for such treatments because of the advanced stage of the disease at the time of diagnosis, or the presence of underlying liver disease (Hong et al., 2006). One major obstacle to the effectiveness of any systemic treatment for HCC is the presence of co-morbid disease ranging from fibrosis to end stage liver cirrhosis.

Liver fibrosis is the scarring process that represents the liver's response to injury and it is a result of chronic inflammatory injury to the liver parenchyma. The primary causes of liver fibrosis are chronic hepatitis virus infection and alcohol and non-alcoholic steatohepatitis. Secondary causes of liver fibrosis include autoimmune conditions and genetic disorders (Friedman, 2013; Mallat and Lotersztajn, 2013). Liver fibrosis ultimately leads to cirrhosis, liver failure, and hepatocellular carcinoma, which results in serious morbidity from the clinical symptoms of cirrhosis (i.e., ascites, variceal bleeding, renal failure and hepatic encephalopathy) and an exceptionally high mortality for patients with HCC that is associated with end-stage liver cirrhosis.

The pathogenesis of liver fibrosis is a process involving the progressive replacement of the hepatic parenchyma with collagen rich extracellular matrix (ECM). In the chronically injured liver, repeated and overlapping phases of inflammation and wound-healing overwhelm the normal regenerative process and cause a net deposition of collagen. Chronic liver injury over an extended period of time leads to the end-stage disease characterized by a profound destruction of the liver lobule with thick bands of fibrotic tissue that bridge hepatic vessels and which surround nodules of regenerating hepatocytes. In gross terms, cirrhosis can be divided into two types: a micro-nodular meshwork of fibrotic bands separating small regenerative nodules and macro-nodular broad bands of fibrotic septae separating larger nodules of varying sizes. This observation suggests a dynamic disease process with several cellular events underlying the cirrhotic and eventual carcinogenic transformation active at the same time.

Recent data suggest that hepatic stellate cells (HSCs) are primarily responsible for fibrosis (Sanchez-Valle, 2012). In the normal liver, HSCs compose from about 5% to about 10% of cells and are located in the subendothelial space between hepatocytes and sinusoidal endothelial cells. During chronic liver disease, HSCs are activated to undergo phenotypic changes from a quiescent (referred to as a normal HSC) to a myofibroblastic phenotype (referred to as an activated HSC). Activation of HSCs is the central event in hepatic fibrogenesis, and it consists of early ("initiation") and late ("perpetuation") phases.

Parenchymal injury promotes activation of Kupffer cells (resident liver macrophages), endothelial cells and platelets, and an influx of leucocytes, resulting in the generation of lipid peroxides, reactive oxygen species, and a number of cytokines, such as TGF-$\beta$, interleukin-1, TGF-$\alpha$, PDGF, and EGF (Ogawa et al., Liu et al., 2011). These factors promote induction of specific sets of transcription factors in HSCs within hours, resulting in the expression of proteins involved in fibrogenesis. Synthesis of TGF-$\alpha$ and TGF-$\beta$ promotes activation of neighboring quiescent HSCs, whereas the release of HGF stimulates regeneration of adjacent hepatocytes. Accumulation of fibrogenic cells results from a high mitogenic and an enhanced capacity to escape from apoptosis. Mitogenicity is stimulated by growth factors, such as PDGF, which has great promitogenic effects, vasoconstrictors, such as thrombin, the matrix metalloproteinase MMP2, and adhesion molecules.

Further, interaction with matrix components, such as collagen I and fibronectin, also plays a crucial role in survival of activated HSCs. The profibrogenic potential of activated HSCs (hepatic myofibroblasts) is due to their capacity to synthesize fibrotic matrix proteins and components that inhibit fibrosis degradation. HSCs express a wide range of matrix metalloproteinases (MMPs), as well as MMP activators that cleave pro-MMP into their active form. In addition, they also produce specific tissue inhibitors of the metalloproteinase family (TIMPs).

Production of MMPs and TIMPs is tightly regulated according to the activation state of HSCs, and it reflects extracellular matrix remodeling during chronic liver injury. At early stages, HSCs express MMP1, MMP2, MMP3, and MMP9 and their activators, but do not produce TIMPs; this allows degradation of normal matrix in the subendothelial space and its substitution by fibrillar collagens. In contrast, fully activated HSCs shut down expression of MMPs and turn on expression of TIMPs, resulting in a dramatic reduction of collagenolytic activity and allowing for the production of fibrotic matrix.

Current therapeutic strategies for reversal of fibrosis and cirrhosis are based on inhibition or attenuation of HSC activation and target a single pathway or phase of the fibrotic progression (Liu et al., 2013; Schuppan and Kim, 2013). Hepatic fibrosis and carcinogenesis, however, is a complex multistep process that results in a large number of heterogeneous molecular changes that can be exploited as potential targets for therapy. An ideal anti-fibrotic drug should be liver specific to avoid adverse effects on extra-hepatic matrix

SUMMARY OF THE INVENTION

The present invention provides at least in part a method for preventing, inhibiting, or treating liver fibrosis in a subject in need of treatment thereof, the method comprising administering to the subject a therapeutically effective amount of one or more 3-halopyruvates, such as 3-bromopyruvate (3-BrPA):

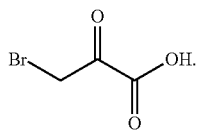

In other aspects, the presently disclosed subject matter provides a method for preventing, inhibiting, or treating cirrhosis, liver failure, and hepatocellular carcinoma in a subject in need of treatment thereof, the method comprising administering to the subject a therapeutically effective amount of a 3-halopyruvate.

In yet other aspects, the presently disclosed subject matter provides a method for inhibiting an activated hepatic stellate cell (HSC) to restore a phenotype that secretes one or more matrix metalloproteinases, the method comprising contacting the activated HSC with an amount of 3-halopyruvate molecules effective for inhibiting the activated HSC.

Another aspect of the invention relates to a method for preventing or treating liver fibrosis in a subject, the method comprising administering to the subject a therapeutically effective amount of a pharmaceutical agent represented in the general formula:

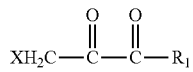

wherein, independently of each occurrence:
X represents a halide, a sulfonate, a carboxylate, an alkoxide, or an amine oxide;
$R_1$ represents OR, H, $N(R'')_2$, C1-C6 alkyl, C6-C12 aryl, C1-C6 heteroalkyl, or C6-C12 heteroaryl;
R" represents H, C1-C6 alkyl, or C6-C12 aryl;
R represents H, alkali metal, C1-C6 alkyl, C6-C12 aryl or C(O)R'; and
R' represents H, C1-C20 alkyl or C6-C12 aryl.

In some embodiments, the subject does not have hepatocellular carcinoma.

In some embodiments, the subject does not have cirrhosis.

In some embodiments, the subject has liver fibrosis that has not progressed beyond stage F3 in the METAVIR fibrosis score.

In some embodiments, the subject has liver fibrosis that has not progressed beyond stage 3 in the Knodell histology activity index.

In some embodiments, the subject has liver fibrosis that has not progressed beyond stage 3 in the Scheuer score.

In some embodiments, the subject has liver fibrosis that has not progressed beyond stage 4 in the Ishak score.

In some embodiments, the subject does not have liver fibrosis.

In some embodiments, the subject has been diagnosed with one or more of the following: hepatitis, alcoholic hepatitis, viral hepatitis, hepatitis B, hepatitis C, hepatitis D, liver steatosis, fatty liver disease (FLD), nonalcoholic fatty liver disease (NAFLD), nonalcoholic steatohepatitis (NASH), alcoholic steatosis, alcoholic steatohepatitis, alcoholic liver disease, Budd-Chiari syndrome, hemochromatosis, Wilson's disease, alpha 1-antitrypsin deficiency, glycogen storage disease, glycogen storage disease type II, glycogen storage disease type IV, autoimmune hepatitis, primary biliary cirrhosis, secondary biliary irrhosis, primary sclerosing cholangitis, cystic fibrosis, lysosomal acid lipase deficiency, galactosemia, history of alcohol abuse, alcoholism, history of drug abuse, or drug addiction.

In some embodiments, the subject has been diagnosed with hepatitis.

In some embodiments, the subject has been diagnosed with viral hepatitis.

In some embodiments, the subject has been diagnosed with liver steatosis.

In some embodiments, X represents F, Cl, Br, or I;
$R_1$ represents OR; and
R represents H, Na, or K.

In some embodiments, wherein X represents Br;
$R_1$ represents OR; and
R represents H, Na, or K.

In some embodiments, the subject is human.

In some embodiments, the subject is non-human.

Another aspect of the invention relates to a method of inhibiting an activated hepatic stellate cell (HSC) by contacting the activated HSC with an effective amount of 3-bromopyruvate.

In some embodiments, said effective amount of 3-bromopyruvate is not toxic to said activated hepatic stellate cell.

In some embodiments, said effective amount of 3-bromopyruvate inhibits the activated hepatic stellate cell after the 3-bromopyrate molecules are no longer present in the cell.

In some embodiments, the methods are performed in vitro, in vivo, or ex vivo.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
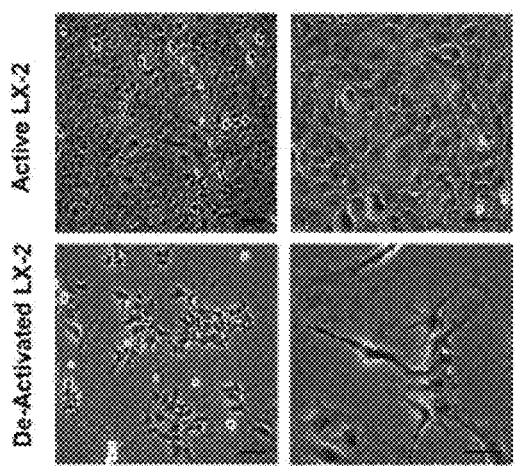
FIG. 1 contains three panels, (A)-(C), depicting generation of de-activated LX-2 using geltrex culture conditions. Panel (A) depicts morphology of de-activated LX-2 cells as compared to aLX-2 cells. Scale=0.5 mm. Panel (B) depicts decrease in the rate of proliferation and Panel (C) shows expression of genes related to invasiveness and motility.
Figure 1:
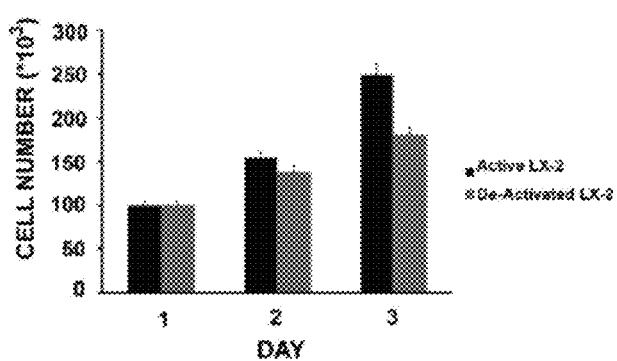
Figure 1:
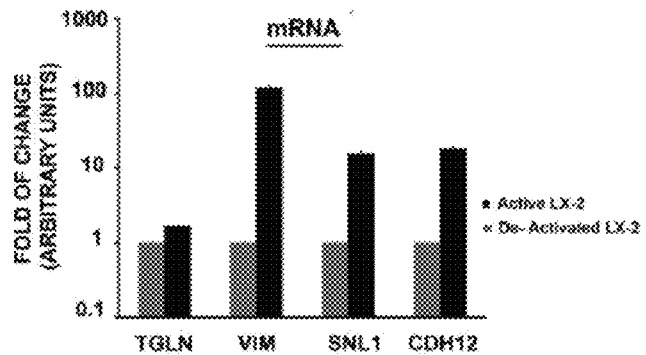

It has been determined herein that 3-halopyruvates (e.g., 3-BrPA) can be administered to reverse the disease processes that causes liver fibrosis. Specifically, it has been shown that 3-BrPA can convert diseased, activated HSCs, which proliferate and over-secrete the matrix proteins that cause fibrosis, into healthy, inhibited HSCs, which are less proliferative and secrete proteinases that reverse fibrosis. This result was unexpected for multiple reasons. First, 3-halopyruvates are toxic to cells, and their primary medical value was thought to stem from their toxicity, which is particularly useful in oncological applications. Second, 3-halopyruvates are known to inhibit glycolysis, and thus, they were believed to preferentially target cancer cells, which rely more heavily on glycolysis for energy than other cells, which rely more heavily on oxidative phosphorylation. Thus, the present application discloses (1) a previously unknown therapeutic effect for 3-halopyruvates, and (2) a previously unknown sensitivity to 3-halopyruvates by cells that are not abnormally dependent on glycolysis. This discovery, as disclosed herein, enables the use of 3-halopyruvates in the treatment and prevention of liver fibrosis and diseases related to liver fibrosis, including cirrhosis and HCC.

The present invention is based at least in part on the discovery that, when administered at non-toxic concentrations, 3-halopyruvates cause activated HSCs to secrete matrix metalloproteinases that break down fibrotic matrix, thereby restoring a beneficial phenotype to previously-aberrant cells. This result is important because 3-halopyruvates do not merely impede fibrosis-causing HSCs—they confer a phenotype that reverses fibrosis. Thus, this application demonstrates that 3-halopyruvates can display a previously unknown therapeutic effect that improves cell function rather than killing the cell. Further, the result is particularly significant because HSCs are not known to rely on glycolysis to a similar extent as cancer cells Thus, this application demonstrates that 3-halopyruvates can display a therapeutic effect on cells that are not distinctively reliant on the glycolysis pathway that the drug disrupts.

A. Definitions

The articles "a" and "an" are used herein to refer to one or to more than one (i.e., to at least one) of the grammatical object of the article. By way of example, "an element" means one element or more than one element.

The terms "3-bromopyruvate," "3-BrPA," or "3-halopyruvate" as used herein refer to compounds, analogs of compounds, derivatives of compounds, prodrugs of compounds, metabolites of compounds, and salts of compounds represented by the general formula:

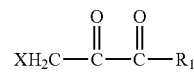

wherein, independently of each occurrence: X represents a halide, a sulfonate, a carboxylate, an alkoxide, or an amine oxide; $R_1$ represents OR, H, $N(R'')_2$, C1-C6 alkyl, C6-C12 aryl, C1-C6 heteroalkyl, or C6-C12 heteroaryl; R" represents H, C1-C6 alkyl, or C6-C12 aryl; R represents H, alkali metal, C1-C6 alkyl, C6-C12 aryl or C(O)R'; and R' represents H, C1-C20 alkyl or C6-C12 aryl.

The term "administering" means providing a pharmaceutical agent or composition to a subject, and includes, but is not limited to, administering by a medical professional and self-administering.

The term "cirrhosis" means the impairment of liver function caused by fibrotic tissue that reduces the flow of blood through the liver.

The terms "fibrosis" and "liver fibrosis" means the deposition of excess extracellular matrix in the liver.

The terms "hepatic stellate cell" and "HSC" as used herein refer to normal HSCs, active HSCs, activated HSCs, resting HSCs, quiescent HSCs, inactive HSCs, inactivated HSCs, inhibited HSCs, parent HSCs, and myofibroblasts of HSC origin. HSCs and myofibroblasts of HSC origin are described in Friedman, S. L., Physiol Rev. 88:125 (2008). The terms "hepatic stellate cell" and "HSC" do not refer to progenitor cells that lack the characteristics of a HSC such as retinoid storage as described in Friedman. The terms "hepatic stellate cell" and "HSC" do not refer to cancer cells, such as neoplastic cells or metastatic cells.

The terms "activated hepatic stellate cell" and "active hepatic stellate cell" as used herein refers to a HSC that can be characterized by one or more of the following changes relative to the prior state of the activated HSC or relative to one of the activated HSC's parent HSCs: increased proliferation propensity, increased expression of one or more matrix metalloproteinase (MMP), increased expression of MMP1, MMP2, MMP3, and/or MMP9, increased expression of an MMP activator, increased expression of a tissue inhibitor of the metalloproteinase family (TIMP), increased expression of α-smooth muscle actin (α-SMA), increased expression of cytokeratin-18 (CK-18), increased expression of vimentin, increased expression of cadherin-12, and/or increased expression of a SNL1 gene product.

The term "fully activated hepatic stellate cell" refers to an activated HSC that has reduced expression of one or more MMP relative to a prior state of the activated HSC or an activated, parent HSC. Thus, a fully activated HSC may be characterized by the reduced expression of MMP-2 relative to its prior activated state or relative to the state of an activated, parent HSC. Similarly, a fully activated HSC may be characterized by the reduced expression of MMP-9 relative to its prior activated state or relative to the state of an activated, parent HSC.

The terms "inhibited HSC" and "inactivated HSC" as used herein refer to an activated HSC that has reversed one or more of the characteristics of an activated HSC or a fully activated HSC relative to a prior state of the inhibited HSC or relative to the prior state of one of the inhibited HSC's activated, parent HSCs. For fully activated HSCs, an inhibited HSC may be characterized by the increased expression of one or more MMP relative to its prior fully activated state or the state of a fully activated parent HSC. Thus, some inhibited HSCs are characterized by an increased expression of MMP-2 relative to a prior fully activated state. Similarly, some inhibited HSCs are characterized by an increased expression of MMP-9 relative to a prior fully activated state.

A "normal hepatic stellate cell" is a HSC that displays none of the characteristics described for an activated HSC.

The term "parent HSC" as used herein refers to every HSC from which a HSC has descended by mitosis. Thus, an HSC is a parent for its daughter HSC and for its daughters' daughters.

The terms "resting HSC," "quiescent HSC," and "inactive HSC" as used herein may refer to either a normal HSC or an inhibited HSC.

The term "inhibit" or "inhibits" means to decrease, suppress, attenuate, diminish, arrest, or stabilize the development or progression of a disease, disorder, or condition, the activity of a biological pathway, or a biological activity, such as the growth of a solid malignancy, e.g., by at least 10%, 20%, 30%, 40%, 50%, 60%, 70%, 80%, 90%, 95%, 98%, 99%, or even 100% compared to an untreated control subject, cell, biological pathway, or biological activity or compared to the target, such as a growth of a solid malignancy, in a subject before the subject is treated. By the term "decrease" is meant to inhibit, suppress, attenuate, diminish, arrest, or stabilize a symptom of a cancer disease, disorder, or condition. It will be appreciated that, although not precluded, treating a disease, disorder or condition does not require that the disease, disorder, condition or symptoms associated therewith be completely eliminated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Pharmaceutically-acceptable salts" refers to the relatively non-toxic, inorganic and organic acid addition salts of compounds.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

A "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

The term "subject in need thereof" means a subject identified as in need of a therapy or treatment.

The terms "systemic administration," "administered systemically," "peripheral administration," and "administered peripherally" mean the administration of a compound, drug or other material other than directly into the central nervous system, such that it enters the patient's system and, thus, is subject to metabolism and other like processes, for example, subcutaneous administration.

The term "therapeutic agent" or "pharmaceutical agent" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents is known in the art and may be identified by their effects. Certain therapeutic agents are capable of regulating red cell proliferation and differentiation. Examples include chemotherapeutic nucleotides, drugs, hormones, non-specific (e.g. non-antibody) proteins, oligonucleotides (e.g., antisense oligonucleotides that bind to a target nucleic acid sequence (e.g., mRNA sequence)), peptides, and peptidomimetics.

The term "therapeutic effect" refers to a local or systemic effect in animals, particularly mammals, and more particularly humans, caused by a pharmacologically active substance.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The term "treating" a disease in a subject or "treating" a subject having a disease refers to subjecting the subject to a pharmaceutical treatment, e.g., the administration of a drug, such that at least one symptom of the disease is decreased, prevented from worsening, or delayed from worsening.

The term "viral hepatitis" refers to hepatitis A, hepatitis B, hepatitis C, hepatitis D, and hepatitis E.

B. Effect of 3-Halopyruvates on Hepatic Stellate Cells

Liver cirrhosis or fibrosis is a chronic liver condition that is a major cause for the development of the primary liver cancer, hepatocellular carcinoma (HCC). The principal mechanisms underlying the process of fibrogenesis are thought to include uncontrolled, activation of the hepatic stellate cells (HSCs), which results in the prolonged secretion of extracellular matrix proteins (ECMs, including collagen) contributing to the formation of fibroids, eventually causing cirrhosis.

The presently disclosed subject matter provides, in some embodiments, that inhibiting activated-HSCs prevents fibrosis/cirrhosis and the development of the related HCC. To date, no energy blocker or antimetabolite has been shown to inhibit activated HSCs without causing toxicity. Energy blockers, in general, are cytotoxic due to the lack of control over their intracellular-bioavailability. The presently disclosed methods use low doses (non-cytotoxic concentrations) of the pyruvate analog 3-bromopyruvate (3-BrPA) to inhibit activated-HSCs. Notably, the presently disclosed methods do not cause any toxicity, indicating the safety of this approach in preserving or protecting normal HSCs. Further, the inhibition of activated-HSCs has been found to be stable and does not change even after the withdrawal of 3-BrPA. Accordingly, the unexpected antifibrotic effects of 3-BrPA has major implications in the control or treatment of liver fibrosis.

Accordingly, in some embodiments, the presently disclosed subject matter provides a method for preventing, inhibiting, or treating liver fibrosis in a subject in need of treatment thereof, the method comprising administering to the subject a therapeutically effective amount of a 3-halopyruvate, such as 3-BrPA:

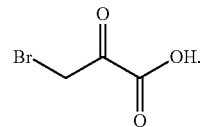

The subject in need of treatment includes a subject having liver fibrosis, at risk of having liver fibrosis, or suspected of having liver fibrosis. The subject treated by the presently disclosed methods in their many embodiments is desirably a human subject, although it is to be understood that the methods described herein are effective with respect to all vertebrate species, which are intended to be included in the term "subject." Accordingly, the subject can be human or non-human.

In particular embodiments, administrating a therapeutically effective amount of a 3-halopyruvate promotes the inhibition of at least one activated HSC. As used herein, the term "inhibition" means to reverse one or more characteristics of that distinguish either an activated HSC from a normal HSC or a fully activated HSC from an activated HSC. Therefore, the inhibition of an activated HSC means that the activated HSC changes to an inhibited HSC as seen by its cell morphology, biochemistry, cellular or molecular markers, and the like.

Importantly, the therapeutically effective amount of a 3-halopyruvate is not cytotoxic to the at least one activated HSC or to the inhibited HSC. As used herein, the term "cytotoxic" means relating to or producing a toxic effect on a cell. For example, administration of a concentration of 3-BrPA that is cytotoxic is a concentration that can kill cells in the subject. As another example, a concentration of 3-BrPA that is "not cytotoxic" does not kill cells when administered to a subject. As used herein, the same definitions of "cytotoxic" and "not cytotoxic" apply under in vitro or ex vivo conditions when a 3-halopyruvate molecule is contacted with a cell. As provided herein below, the activated HSC's inhibited-phenotype has been confirmed by biochemical and cellular markers, while the non-toxic effects were validated by standard methods, such as a viability assay and a proliferation-assay.

The inhibition of the at least one activated HSC is evidenced by at least one characteristic selected from the group consisting of a change in cell morphology, an increase in extracellular secretion of MMPs, and a decrease in the levels of α-SMA. Further, in some embodiments, the at least one inhibited HSC does not lose its inhibited phenotype after the 3-halopyruvate is no longer administered. "No longer administered" means that the 3-halopyruvate is no longer being administered to the subject and/or 3-halopyruvate and/or its metabolites have been cleared, e.g., excreted, by the subject and are no longer at therapeutic levels in the subject.

Further, in some embodiments, administering to the subject a therapeutically effective amount of 3-halopyruvate prevents development of and/or treats a liver condition selected from the group consisting of cirrhosis, liver failure, and HCC. In yet further embodiments, administering to the subject a therapeutically effective amount of 3-halopyruvate prevents formation of excess collagen in the liver of the subject.

In other embodiments, the presently disclosed subject matter provides a method for preventing, inhibiting, or treating cirrhosis, liver failure, and HCC in a subject in need of treatment thereof, the method comprising administering to the subject a therapeutically effective amount of 3-BrPA. The subject in need of treatment includes a subject having cirrhosis, liver failure, and/or HCC, at risk of having cirrhosis, liver failure, and/or HCC, or suspected of having cirrhosis, liver failure, and/or HCC. As provided hereinabove, cirrhosis, liver failure, and HCC can develop from liver fibrosis.

In particular embodiments, administrating a therapeutically effective amount of 3-halopyruvate to treat the cirrhosis, liver failure, and HCC promotes the inhibition of at least one activated HSC. In some embodiments, the therapeutically effective amount of 3-halopyruvate is not cytotoxic to the at least one activated HSC or to the inhibited HSC. In other embodiments, the inhibition of the at least one activated HSC is evidenced by at least one characteristic selected from the group consisting of a change in cell morphology, an increase in extracellular secretion of MMPs, and a decrease in the levels of α-SMA. In yet other embodiments, the at least one inhibited HSC does not lose its inhibited phenotype after the 3-halopyruvate is no longer administered.

In other embodiments, the presently disclosed subject matter provides a method for promoting the inhibition of an activated HSC, the method comprising contacting the activated HSC with an amount of one or more 3-halopyruvate molecules effective for inhibiting the activated HSC.

By "contacting," it is meant any action that results in at least one 3-halopyruvate molecule physically contacting at least one cell. It thus may comprise exposing the cell(s) to the 3-halopyruvate molecule in an amount sufficient to result in contact of at least one 3-halopyruvate molecule with at least one cell. The method can be practiced in vitro or ex vivo by introducing, and preferably mixing, the 3-halopyruvate molecule and cell in a controlled environment, such as a culture dish or tube. The method can be practiced in vivo, in which case contacting means exposing at least one cell in a subject to at least one 3-halopyruvate molecule, such as administering the 3-halopyruvate to a subject via any suitable route. According to the presently disclosed subject matter, contacting may comprise introducing, exposing, and the like, the 3-halopyruvate molecule at a site distant to the cell to be contacted, and allowing the bodily functions of the subject, or natural (e.g., diffusion) or man-induced (e.g., swirling) movements of fluids to result in contact of the 3-halopyruvate molecule and cell(s). In some embodiments, the cell is an activated HSC. In some embodiments, the method may inhibit an activated HSC in vitro, in vivo, or ex vivo.

In particular embodiments, contacting the activated HSC with an effective amount of 3-halopyruvate is not cytotoxic to the activated HSC or to the inhibited HSC. In other embodiments, the at least one inhibited HSC does not lose its inhibited phenotype after the at least one inhibited HSC is no longer in contact with the 3-halopyruvate. In some embodiments, contacting the activated HSC with an effective amount of 3-halopyruvate occurs in vitro, in vivo, or ex vivo. In some embodiments, the presently disclosed methods inhibit at least about 10%, 15%, 20%, 25%, 30%, 35%, 40%, 45%, 50%, 55%, 60%, 65%, 70%, 75%, 80%, 85%, 90%, 95%, or even 100% of activated HSCs.

C. Therapeutic Indications for 3-Halopyruvates 3-halopyruvates may be used to treat subjects with activated hepatic stellate cells (HSCs), subjects with liver fibrosis, subjects with liver fibrosis that has progressed to cirrhosis, subjects with hepatocellular carcinoma (HCC), and/or subjects at risk of developing liver fibrosis, cirrhosis, and/or HCC.

3-halopyruvates inhibit the progression of fibrosis, which can cause cirrhosis and/or HCC. Thus, the presently disclosed subject matter provides a method for preventing, reducing the incidence of, delaying the onset of, or reducing the severity of liver fibrosis in a subject who displays no liver cirrhosis but is at risk for developing cirrhosis and/or HCC. Additionally, the presently disclosed subject matter provides a method for preventing, reducing the incidence of, delaying the onset of, or reducing the severity of liver fibrosis in a subject who displays no HCC but is at risk for developing HCC.

Because they inhibit fibrosis, 3-halopyruvates may be administered prophylactically to reduce the incidence of fibrosis and related diseases, including cirrhosis and HCC. For example, 3-halopyruvates may be administered to inhibit fibrosis in subjects who are prescribed medications that affect the liver and subjects who may otherwise be exposed to drugs, chemicals, or trauma that may affect the liver. Thus, the presently disclosed subject matter provides a method for preventing, reducing the incidence of, delaying the onset of, or reducing the severity of liver fibrosis in a subject who displays no liver fibrosis but is at risk for developing fibrosis, cirrhosis, and/or HCC.

3-halopyruvates cause activated HSCs, which proliferate and secrete fibrosis-promoting molecules, to proliferate less rapidly and secrete molecules that degrade fibrotic matrix proteins. Thus, the presently disclosed subject matter provides a method for preventing, reducing the incidence of, delaying the onset of, or reducing the severity of liver fibrosis in a subject who displays no fibrosis but has activated HSCs.

3-halopyruvates cause HSCs to secrete molecules that degrade fibrotic matrix proteins, which can reduce the incidence of fibrosis and diseases caused by fibrosis, including cirrhosis and HCC, even if a subject has no fibrosis and no activated HSCs. Such prophylactic use may be beneficial for subjects at risk for developing fibrosis, such as subjects with fatty liver (steatosis), liver inflammation (hepatitis), congenital diseases that affect the liver, metabolic diseases that affect the liver, autoimmune disease that affect the liver, and/or acute or chronic exposure to drugs or chemicals that affect the liver.

Additionally, the presently disclosed subject matter provides a method for preventing, reducing the incidence of, delaying the onset of, or reducing the severity of liver fibrosis in a subject who is at risk for developing fibrosis, cirrhosis, and/or HCC but has no activated HSCs and no fibrosis. In some aspects, the presently disclosed subject matter provides a method for preventing, reducing the incidence of, delaying the onset of, reducing the severity of, or treating liver fibrosis in a subject diagnosed with one or more of the following: hepatitis, alcoholic hepatitis, viral hepatitis, hepatitis B, hepatitis C, hepatitis D, jaundice, steatosis, fatty liver disease, nonalcoholic fatty liver disease, nonalcoholic steatohepatitis, alcoholic steatosis, alcoholic steatohepatitis, alcoholic liver disease, Budd-Chiari syndrome, metabolic diseases, hemochromatosis, Wilson's disease, alpha 1-antitrypsin deficiency, glycogen storage diseases, glycogen storage disease type II, glycogen storage disease type IV, autoimmune disorders, autoimmune hepatitis, primary biliary cirrhosis, secondary biliary cirrhosis, primary sclerosing cholangitis, certain congenital defects, cystic fibrosis, lysosomal acid lipase deficiency, galactosemia, history of alcohol abuse, alcoholism, history of drug abuse, or drug addiction.

D. Characterization of Liver Fibrosis

Liver fibrosis consists of many different disease-states, which may be characterized by liver needle biopsy, hepatic ultrasound, transient ultrasound elastography, magnetic resonance elastography, and/or one of many different scoring systems including the Scheuer, Ludwig, Knodell, Ishak, METAVIR, International Association for Study of the Liver, FibroSure, HepaScore, Forns Index, FIB-4, FibroIndex, aspartate aminotransfeerase-to-platelet ration index and/or other tests. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include α-2-macroglobulin, haptoglobin, gamma globulin, apolipoprotein A, and gamma glutamyl transpeptidase.

The METAV1R scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell histology activity index (scores of periportal necrosis, lobular necrosis, portal inflammation, fibrosis, and overall disease activity). The definitions of each stage in the METAVIR system are as follows: score: F0, no fibrosis; score: F1, stellate enlargement of portal tract but without septa formation; score: F2, enlargement of portal tract with rare septa formation; score: F3, numerous septa without cirrhosis; and score: F4, cirrhosis. Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis.

In some aspects, the subject matter provides a method for treating or reducing the severity of liver fibrosis in a subject who has not progressed beyond stage F3 in the METAVIR scoring system. In some aspects, the subject matter provides a method for treating or reducing the severity of liver fibrosis in a subject who has not progressed beyond stage F2 in the METAVIR scoring system. In some aspects, the subject matter provides a method for treating or reducing the severity of liver fibrosis in a subject who has not progressed beyond stage F1 in the METAVIR scoring system. In some aspects, the subject matter provides a method for preventing, reducing the incidence of, delaying the onset of, reducing the severity of, or treating liver fibrosis in a subject who has not progressed beyond stage F0 in the METAVIR scoring system.

In the Knodell histology activity index, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) *Hepatol.* 1:431.

In some aspects, the subject matter provides a method for treating or reducing the severity of liver fibrosis in a subject who has not progressed beyond stage 3 in the Knodell scoring system. In some aspects, the subject matter provides a method for treating or reducing the severity of liver fibrosis in a subject who has not progressed beyond stage 2 in the Knodell scoring system. In some aspects, the subject matter provides a method for treating or reducing the severity of liver fibrosis in a subject who has not progressed beyond stage 1 in the Knodell scoring system. In some aspects, the subject matter provides a method for preventing, reducing the incidence of, delaying the onset of, reducing the severity of, or treating liver fibrosis in a subject who has not progressed beyond stage 0 in the Knodell scoring system. Knodell (1981) *Hepatol.* 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) *J. Hepatol.* 13:372.

In some aspects, the subject matter provides a method treating or reducing the severity of liver fibrosis in a subject who has not progressed beyond stage 3 in the Scheuer scoring system. In some aspects, the subject matter provides a method for treating or reducing the severity of liver fibrosis in a subject who has not progressed beyond stage 2 in the Scheuer scoring system. In some aspects, the subject matter provides a method for treating or reducing the severity of liver fibrosis in a subject who has not progressed beyond stage 1 in the Scheuer scoring system. In some aspects, the subject matter provides a method for preventing, reducing the incidence of, delaying the onset of, reducing the severity of, or treating liver fibrosis in a subject who has not progressed beyond stage 0 in the Scheuer scoring system. Scheuer (1991) *J. Hepatol.* 13:372.

The Ishak scoring system is described in Ishak (1995) *J. Hepatol.* 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

In some aspects, the subject matter provides a method for treating or reducing the severity of liver fibrosis in a subject who has not progressed beyond stage 5 in the Ishak scoring system. In some aspects, the subject matter provides a method for treating or reducing the severity of liver fibrosis in a subject who has not progressed beyond stage 4 in the Ishak scoring system. In some aspects, the subject matter provides a method for treating or reducing the severity of liver fibrosis in a subject who has not progressed beyond stage 3 in the Ishak scoring system. In some aspects, the subject matter provides a method for treating or reducing the severity of liver fibrosis in a subject who has not progressed beyond stage 2 in the Ishak scoring system. In some aspects, the subject matter provides a method for treating or reducing the severity of liver fibrosis in a subject who has not progressed beyond stage 1 in the Ishak scoring system. In some aspects, the subject matter provides a method for preventing, reducing the incidence of, delaying the onset of, reducing the severity of, or treating liver fibrosis in a subject who has not progressed beyond stage 0 in the Ishak scoring system. Ishak (1995) *J. Hepatol.* 22:696.

E. 3-Halopyruvate Compositions

In one aspect, the invention provides selective inhibitors of ATP production represented in the general formula:

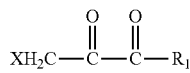

wherein X represents a halide, a sulfonate, a carboxylate, an alkoxide, or an amine oxide. In certain embodiments, X is a halide selected from the group consisting of: fluoride, bromide, chloride, and iodide. In one embodiment, the inhibitor is a 3-halopyruvate. In certain other embodiments, the 3-halopyruvate is selected from the group consisting of: 3-fluoropyruvate, 3-chloropyruvate, 3-bromopyruvate and 3-iodopyruvate. In one embodiment, the 3-halopyruvate is 3-bromopyruvate. In other embodiments, X is a sulfonate is selected from the group consisting of: triflate, mesylate and tosylate. In yet another embodiment, X is an amine oxide is dimethylamine oxide. In certain embodiments $R_1$ represents OR, H, N(R")$_2$, C1-C6 alkyl, C6-C12 aryl, C1-C6 heteroalkyl, or a C6-C12 heteroaryl. Independently, in other embodiments, R" represents H, C1-C6 alkyl, or C6-C12 aryl. Independently, in still other embodiments, R represents H, alkali metal, C1-C6 alkyl, C6-C12 aryl or C(O)R'; and R' represents H, C1-C20 alkyl or C6-C12 aryl.

In a preferred embodiment, the invention further provides inhibitors of ATP production represented in general formula:

wherein X represents a halide, a sulfonate, a carboxylate, an alkoxide, or an amine oxide. In certain embodiments, X is a halide selected from the group consisting of: fluoride, bromide, chloride, and iodide. In one embodiment, the inhibitor is a 3-halopyruvate. In certain embodiments, the 3-halopyruvate is selected from the group consisting of: 3-fluoropyruvate, 3-chloropyruvate, 3-bromopyruvate and 3-iodopyruvate. In one embodiment, the 3-halopyruvate is 3-bromopyruvate. In other embodiments, X is a sulfonate is selected from the group consisting of: triflate, mesylate and tosylate. In yet another embodiment, X is an amine oxide is dimethylamine oxide.

In some embodiments, the 3-halopyruvate may be employed in combination with one or more carriers to allow more stability, different releasing properties in vivo, targeting to a specific site, or any other desired characteristic that will allow more effective delivery of the 3-halopyruvate compound to a subject or a target in a subject. Examples of carriers include, but are not limited to, cyclodextrins, liposomes, nanoparticles, microspheres, and microbubbles.

The 3-halopyruvate, either alone or in combination with one or more carriers, can be dispersed in a physiologically compatible carrier. As used herein, "physiologically compatible carrier" refers to a physiologically acceptable diluent including, but not limited to water, phosphate buffered saline, or saline, and, in some embodiments, includes another adjuvant.

Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight polypeptides (less than about 10 residues); proteins, such as albumin, gelatin or immunoglobulins; hydrophilic polymers, such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG.

In another embodiment, the 3-halopyruvate can be administered in combination with an adjuvant. Additional adjuvants may include, but are not limited to, monophosphoryl lipid A (MPL); LTK63, dimethyl dioctadecyl-ammonium bromide (DDA), lipophilic quaternary ammonium salt-DDA, Trehalose dimycolate and synthetic derivatives, DDA-MPL, DDA-TDM, DDA-TDB, IC-31, aluminum salts, aluminum hydroxyide, aluminum phosphate, potassium aluminum phosphate, Montanide ISA-51, ISA-720, microparticles, immuno stimulatory complexes, liposomes, virosomes, virus-like particles, CpG oligonucleotides, cholera toxin, heat-labile toxin from *E. coli*, lipoproteins, dendritic cells, IL-12, GM-CSF, nanoparticles; a combination of soybean oil, emulsifying agents, and ethanol to form a nanoemulsion; ASO4, ZADAXIN, or combinations thereof.

Compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

As described above, in certain embodiments, the presently disclosed subject matter also includes combination therapies. These additional agents may be administered separately, as part of a multiple dosage regimen, or they may be part of a single dosage form in a single composition.

By "in combination with" is meant the administration of one or more 3-halopyruvates with one or more therapeutic agents either simultaneously, sequentially, or a combination thereof. Therefore, a subject administered a combination of one or more 3-halopyruvates and/or therapeutic agents, can receive the 3-halopyruvates as described herein, and one or more therapeutic agents at the same time (i.e., simultaneously) or at different times (i.e., sequentially, in either order, on the same day or on different days), so long as the effect of the combination of both agents is achieved in the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered agent is not diminished by the sequential, simultaneous or separate administration of the subsequent agent(s).

The presently disclosed compositions comprising 3-BrPA can be administered using a variety of methods known in the art depending on the subject and the particular disease, disorder, or condition being treated. The administering can be carried out by, for example, intravenous infusion; injection by intravenous, intraperitoneal, intracerebral, intramuscular, intraocular, intraarterial or intralesional routes; or topical or ocular application.

More particularly, as described herein, 3-BrPA can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

More particularly, pharmaceutical compositions for oral use can be obtained through combination of 3-BrPA with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of 3-BrPA compositions, e.g., dosage, or different combinations of doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, 3-BrPA can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include cyclodextrins, polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(-)-3-hydroxybutyric acid (EP 133,988A).

Pharmaceutical compositions for parenteral administration include aqueous solutions of 3-BrPA. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of 3-BrPA compositions include fatty oils, such as sesame oil, or synthetic fatty acid esters, such as ethyl oleate or triglycerides, or liposomes. Optionally, the suspension also can contain suitable stabilizers or agents that increase the solubility of the compositions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

Regardless of the route of administration selected, the presently disclosed 3-BrPA compositions are formulated into pharmaceutically acceptable dosage forms such as described herein or by other conventional methods known to those of skill in the art.

F. Therapeutic Methods

Actual dosage levels of the active ingredients in the presently disclosed compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular composition comprising the 3-BrPA of the presently disclosed subject matter, the route of administration, the time of administration, the duration of the treatment, other drugs and/or materials used in combination with the particular 3-BrPA employed, the age, sex, weight, condition, general health and prior medical history of the patient being treated, and like factors well known in the medical arts.

A physician having ordinary skill in the art can readily determine and prescribe the effective amount of 3-BrPA required. Accordingly, the dosage range for administration will be adjusted by the physician as necessary.

Generally, doses of 3-BrPA will range from about 0.0001 to about 1000 mg per kilogram of body weight of the subject. In certain embodiments, the dosage is between about 1 μg/kg and about 500 mg/kg, more preferably between about 0.01 mg/kg and about 50 mg/kg. For example, in certain embodiments, a dose can be about 1, 5, 10, 15, 20, or 40 mg/kg.

EXEMPLIFICATION

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Summary

Liver fibrosis and cirrhosis result from uncontrolled secretion and accumulation of extracellular matrix (ECM) proteins by hepatic stellate cells (HSCs) that are activated by liver injury and inflammation. Despite progress in understanding the biology and the identification of targets for treating fibrosis, the development of an effective therapy still remains elusive. Since an uninterrupted supply of intracellular energy is critical for the activated-HSCs to maintain constant synthesis and secretion of ECM, it hypothesized that interfering with energy metabolism could affect ECM secretion. Here we report that a sub-lethal dose of the energy blocker, 3-bromopyruvate (3-BrPA) facilitates phenotypic alteration of activated LX-2 (a human hepatic stellate cell line), into a less-active form. This treatment-dependent reversal of activated-LX2 cells was evidenced by a reduction in α-smooth muscle actin (α-SMA) and collagen secretion, and an increase in activity of matrix metalloproteases. Mechanistically, 3-BrPA-dependent antifibrotic effects involved the down-regulation of ATPSE, a mitochondrial metabolic enzyme, and an up-regulation of glycolysis, as evident by elevated levels of lactate dehydrogenase, lactate production and its transporter, MCT4. Finally, the antifibrotic effects of 3-BrPA were validated in vivo in a mouse model of carbon tetrachloride-induced liver fibrosis. Results from the histopathology, histochemical staining for collagen and α-SMA, and quantification of serum cytokines established that 3-BrPA promoted antifibrotic effects in vivo.

Taken together, these data indicate that selective disruption of energy metabolism in activated-HSCs blocked the progression of fibrosis suggesting its potential as a novel therapeutic strategy for treating liver fibrosis.

Introduction

Liver fibrosis and cirrhosis occur as a result of chronic inflammatory injury to the liver parenchyma. Irrespective of the primary cause, liver fibrosis eventually leads to cirrhosis and liver failure (Pinzani et al., 2011). Epidemiological data indicate that >70-80% of cirrhotic patients will eventually develop hepatocellular carcinoma (HCC) (Geschwind et al., 2002; Macaron et al., 2010; Okuda, 2007). Many liver diseases can now be controlled or even cured. However, the only treatment for advanced cirrhosis is liver transplantation, a limited and expensive therapy. Novel therapeutic strategies to reverse fibrosis and cirrhosis are urgently needed and would be a revolutionary advancement in the practice of hepatology.

The pathogenesis of liver fibrosis involves the progressive replacement of normal hepatic parenchyma with collagen-rich extracellular matrix (ECM) (Gines et al., 2012). The principle cells responsible for liver fibrosis are hepatic stellate cells (HSCs) (Wu and Zern, 2000). In normal liver, HSCs are quiescent and compose only 5% to 10% of the liver (Friedman, 2008). With liver injury and associated inflammatory cytokine/chemokine release, HSCs transform to a myofibroblast phenotype (activated-HSC/aHSC). In chronic liver injury, frequent and overlapping phases of uncontrolled inflammatory and wound-healing processes result in the constant activation of HSCs leading to increased deposition and decreased degradation of collagen (Ahmad and Ahmad, 2012). In fact, livers with advanced stages of fibrosis have an estimated 4-8 fold more ECM than non-fibrotic livers (Iredale et al., 2013; Wells, 2008). Thus, the HSCs that contribute to the central event (excess accumulation of ECM) in hepatic fibrogenesis would be an ideal target for anti-fibrotic therapy.

In advanced liver fibrosis or cirrhosis, there is an increased energy demand associated with increased synthesis and secretion of ECM (Ganapathy-Kanniappan et al., 2014; Nishikawa et al., 2014). Activated-HSCs are functionally dependent on a constant supply of intracellular ATP to maintain ECM synthesis and secretion. This energy demand provides an opportunity to interfere with the function of aHSCs. Accordingly, medicines that selectively target energy metabolism through the inhibition of ATP production in aHSCs may be an effective therapeutic strategy for prevention of cirrhosis. 3-bromopyruvate (3-BrPA), a pyruvate analog that was developed as an anticancer agent and a potent inhibitor of ATP production, has been validated for the treatment of multiple types of malignancies (Buijs et al., 2009; Buijs et al., 2013; Chapiro et al., 2014; Davidescu et al., 2012; Ganapathy-Kanniappan et al., 2010; Ota et al., 2013; Sanchez-Arago and Cuezva, 2011). 3-BrPA's antineoplastic effect involves the disruption of energy metabolism (Ganapathy-Kanniappan et al., 2009a; Ganapathy-Kanniappan et al., 2009b; Geschwind et al., 2002; Rodrigues-Ferreira et al., 2012) through inhibition of glycolysis and oxidative phosphorylation resulting in induction of ER stress (Ganapathy-Kanniappan et al., 2010) and redox imbalance (Ihrlund et al., 2008). Cellular uptake of 3-BrPA in these cells is dependent on the expression of the Monocarboxylate Transporter (MCT)-1. This transporter is therefore the main determinant of sensitivity to 3-BrPA. Recently, we developed a β-cyclodextrin (β-CD) analog of 3-BrPA which is effective for systemic delivery (Chapiro et al., 2014). The aim of the current study is to determine the effects of a nonlethal dose of 3-BrPA on aHSCs in vitro and in vivo, and to validate that targeting energy metabolism is a rational and viable strategy to treat liver fibrosis.

Example 1: Material and Methods for Examples 2-6

Chemicals, Reagents and Media.

Unless otherwise mentioned, all chemicals including the pyruvate analog, 3-brompyruvate, were purchased from Sigma Aldrich Co., (St. Louis, Mo., USA). Cell culture media, antibiotics and geltrex were procured from Invitrogen/Life Technologies Inc., (Carlsbad, Calif., USA). Chamber slides used for confocal microscopy were purchased from Nalgene/Nunc Inc., (Waltham, Mass., USA). Primary antibodies used for immunoblotting and immunofluorescence were MMP-2, MMP-9 and cytokeratin-18 (CK-18) (Cell Signaling Inc., Danvers, Mass.), Monocarboxylate Transporter (MCT)-4, MCT-1, Adenine tri phosphatase 5E (ATPSE) and lactate dehydrogenase A (LDH-A) (Santa Cruz Biotechnology
Inc., Santa Cruz, Calif.) and α-smooth muscle actin (α-SMA) and anti-leptin antibodies (Sigma Aldrich Co.). Secondary antibodies were purchased from Santa Cruz Biotechnology Inc.

Animals.

Male mice (Balb/C6) 3 to 4 weeks of age were purchased from Charles River laboratories (Wilmington, Mass., USA) and maintained in a temperature-controlled room with an alternating 12 hour dark and light cycle (Wang et al., 2007). Animal studies were performed as approved by the Johns Hopkins University Animal Care and Use Committee. All animal experiments were conducted in accordance with the approved protocol as per the guidelines and regulations of the institute.

Cell Culture.

LX-2, a human stellate cell line, was a gift of Dr. Scott L. Friedman from the Mount Sinai School of Medicine (New York, N.Y., USA). The LX-2 cells when cultured on plastic are active in fibrogenesis (Gaca et al., 2003), and these activated LX-2 cells were used in most experiments. De-activated (quiescent) LX-2 cells prepared by culturing the LX-2 cells on Matrigel (Gaca et al., 2003; Sohara et al., 2002; Troeger et al., 2012) were used as controls. The activated and de-activated LX-2 cells were then cultured in Dulbecco's Modified Eagle's Medium (DMEM) containing 10% FBS, 0.1% antibiotic (Penicillin-Streptomycin) and 0.1% Fungizone on plastic as described previously (Tang et al., 2003). Rat hepatic stellate cells were
isolated and cultured as described previously (Anania et al., 1996). Human primary hepatocytes were obtained from Invitrogen and cultured in William's medium (without phenol red) along with plating and maintenance supplements.

Determination of Nontoxic, Maximum Tolerated Dose (MTD) of 3-BrPA.

To determine the nonlethal, maximum tolerated dose (MTD) of 3-BrPA for activated-LX-2 cells, the cell viability was assessed using either Trypan-blue exclusion or quantification of intracellular ATP level. The later was performed using the Cell-Titer Glo Assay kit (Promega Corp., Madison, Wis.) and the FLUOstar Omega plate reader (BMG Labtech, UK). In brief, cells plated in 96-well flatbottomed opaque plates were treated with different concentrations of 3-BrPA (5 µM, 10 µM, 25 µM and 50 µM) for 24, 48 and 72 hours followed by the quantification of intracellular ATP. The maximum dose of 3-BrPA that allowed more than 50% survival (a concentration <IC50) was selected for further experiments.

Metronomic Therapy for Activated-LX-2 Cells.

To analyze the effect of 3-BrPA on activated-LX-2 cells, the principle of metronomic therapy, a repeated but low, nonlethal dose of 3-BrPA (250$) was adopted. A known number of cells were plated in 6-well plates, 10 cm petri dishes or chamber slides as required and the culture media was replaced with fresh culture media containing the drug(s) on alternative days. The cells were treated for a period of 13 days for immunofluorescence studies and 6 days for all other studies including biochemical analysis. Monotherapy involved treating the cells with 3-BrPA alone or AICAR (0.5 mM) in DMEM with 2.5% FBS. The concentration of AICAR was chosen based on the prior reports (Lim et al., 2012). Combination therapy involved using half of the dose used for the monotherapy of AICAR and 3-BrPA.

Immunofluorescence (Confocal Microscopy).

LX-2 cells were grown in chamber slides in the same media used for culture. They were fixed with 4% formaldehyde for 10 minutes, rapidly rehydrated with Phosphate-buffered saline (PBS) and permeabilized with a 0.20% Triton X-100 solution in PBS for imaging of MCT-1, MCT-4 and ATPSE. The cells were incubated with primary antibodies in PBS for 1 hour at room temperature in a humidified chamber. They were then washed and incubated at room temperature with secondary antibody labeled with Texas Red or FITC (CK-18) for 30 minutes, followed by nuclear staining with DAPI (300 nM) for 1-5 minutes. The slides were mounted with ProLong Gold anti-fade (Invitrogen, USA) mounting media. Images were acquired with the Zeiss 510 Meta LSM Confocal Microscope.

Immunoblotting.

For western blotting, control and treated cells were washed in PBS, lysed in RIPA lysis buffer (Sigma-Aldrich) with a protease inhibitor cocktail and a phosphatase inhibitor cocktails (both from Sigma-Aldrich) at 4° C. using a dounce homogenizer. The lysates were centrifuged at 12,000×g for 15 min at 4° C. to remove any cell debris. The clear supernatants were collected and the protein concentrations were analyzed using a 2-D Quant protein assay Kit (GE Healthcare) as described (Ganapathy-Kanniappan et al., 2009a). In brief, protein samples were resolved on a 4-12% Bis-Tris gel by electrophoresis with MOPS buffer or via 12% Bis-Tris gel electrophoresis with MES running buffer (for low molecular weight targets) and blotted onto PVDF membranes (BioRad, Hercules, Calif., USA) followed by immunoblotting with specific antibodies. Immune complexes were visualized by ECL-detection kit (GE Health Care).

Gelatin Zymography for Matrix Metalloproteinase (MMP) Activity.

The level of MMP activity in the conditioned medium of control and treated LX-2 cells and/or rat HSCs was quantified by gelatin zymography. In brief, upon the completion of drug treatment protocol, media from both control and treated cells were removed, cells were rinsed with PBS and replaced with serum-free DMEM media and cultured overnight at 37° C. prior to the collection of media containing secreted proteins for further analysis. The media thus collected were concentrated using a 3000 Da centrifugal filter (Amicon Inc., Pineville, N.C., USA) at 2500 rpm for 30 minutes at 4° C. and then stored at −80° C. until further analysis. Protein (~10 µg) samples from the conditioned media of control and treated cells were subjected to zymography as described (Kunjithapatham et al., 2014). The MMP activity was visualized as clear bands. The identity of the MMP associated with zymogram signal (activity) was verified by immunoblot analysis.

Determination of mRNA by Real-Time Quantitative Polymerase Chain Reaction.

Gene expression analysis was performed by using qRT-PCR with a sequence detection system (ABI 7900HT; Applied Biosystems, Bedford, Mass., USA). The total RNA was extracted and the cDNA thus synthesized were subjected to qRT-PCR analysis using SYBR Green PCR Kit (Applied Biosystems) for genes associated with invasiveness and motility like Vimentin (VIM), Cadherin-12 (CDH12), Snail (SNAI1), Transgelin (TGN) (31-33) and TaqMan PCR Kit for Coll1α (Mm 00801666_g1). The primers used for respective gene amplification were synthesized by RealTimePrimers.com (Elkins Park, Pa., USA) or Life Technologies (Coll1α):

The primers used were as follows: 5'-TCCAAGTTTGCTGACCTCTC-3' (SEQ ID NO: 1) (forward) and 5'-TCAACGGCAAAGTTCTCTTC-3' (SEQ ID NO: 2) (reverse) for VIM, 5'-TGGATGGACCTTATGTTGCT-3' (SEQ ID NO: 3) (forward) and 5'-AACACCTGTCTTGG-GATCAA-3' (SEQ ID NO: 4) (reverse) for CDH12, 5'-ACCCCACATCCTTCTCACTG-3' (SEQ ID NO: 5) (forward) and 5'-TACAAAAACCCACGCAGACA-3' (SEQ ID NO: 6) (reverse) for SNA1 and 5'-GCAGTC-CAAAATCGAGAAGA-3' (SEQ ID NO: 7) (forward) and 5'-ACCAGCTTGCTCAGAATCAC-3' (SEQ ID NO: 8) (reverse) for TGN. The internal control primer set 18S was used (Applied Biosystems) and the results were also verified with other housekeeping genes such as β-actin and β2-microglobulin (RealTimePrimers.com).

Two Dimensional (2D) Gel Electrophoresis.

For 2D gel electrophoresis the cells were washed in ice-cold PBS and lysed using 2% SDS with protease and phosphatase inhibitors. The lysate was then sonicated at 15% amplitude for 9 seconds and centrifuged to remove any precipitate. Protein samples (20 µg) were subjected to 2D clean up (GE Healthcare Inc., Piscataway N.J., USA) and re-suspended with DeStreak Rehydration solution and loaded on to immobilized pH 3-10 IEF strips (GE Healthcare) and focused for 16 hours from 50V-3000 V. The second dimension SDSPAGE was carried out on 1 mm 4-12% Bis-Tris ZOOM gels for 2 hours at room temperature. The proteins were then transferred on to PVDF membranes for detection by immunoblotting as described elsewhere.

Animal Treatment.

Animal experiments to evaluate the antifibrotic effects of 3-BrPA were designed as described below. Microencapsulated 3-BrPA (β-CD-3-BrPA) used for animal experiments was prepared as described (Chapiro et al., 2014). Mice were randomly divided into control (vehicle-olive oil) group, CCl$_4$ (fibrosis) group, and CCl$_4$+β-CD-3-BrPA (treatment of fibrosis) group. Ten mice received an intra-peritoneal injection of CCl$_4$ biweekly as 100 µL of a 2.5% solution of CCl$_4$ in olive oil per gram body weight. Five of these mice were treated with β-CD-3-BrPA at a dose of 1 mg/kg body weight the day after CCl$_4$ injection. Five control mice received an isovolumetric dose of olive oil as that of the CCl$_4$. The biweekly treatment regimen was carried out for 4 weeks at the end of which the animals were sacrificed. At the time of sacrifice the blood was obtained from the animal for serum analysis and the liver was removed and divided into two portions: a) fixed in 10% buffered formaldehyde and embedded in paraffin; b) homogenized in RIPA buffer and stored at −80° C. for biochemical assays.

Histology and Immunofluorescence.

Liver tissues from different animal groups were fixed in 10% phosphate-buffered formalin (Polysciences, Warrington, Pa.), dehydrated with graded ethanol, embedded in wax (Paraplast Plus; McCormick Scientific, Richmond, Ill.), sliced at 5 mm, mounted on slides, and oven dried and deparaffinized and subjected to hematoxylin-eosin staining as described (Ganapathy-Kanniappan et al., 2012). The images were captured using high-resolution scanner system (Aperio®, Leica Microsystems Inc., Vista, Calif.). The digitized slides were then assessed using the Aperio ImageScope® viewing software. Immunofluorescence staining for the profibrotic marker, α-SMA was performed as described with few modifications. In brief, prior to primary antibody incubation, tissue sections were subjected to deparaffinization, antigen retrieval and blocking with 10% goat serum. Rest of the protocol for immune staining was performed as described before. The slides were viewed with fluorescent microscopy, and the images were acquired with Zeiss 510 Meta LSM Confocal Microscope.

Collagen Staining.

Tissue sections were deparaffinized in xylene followed by rehydration through graded series of alcohol followed by staining for collagen using Masson's Trichrome stain (Sigma Aldrich, St. Louis, Mo.) or Sirius Red stain (PolySciences. Inc Warrington, Pa.). For in vitro studies, the LX-2 cells were grown in chamber slides containing appropriate growth medium. They were fixed with 4% formaldehyde for 10 minutes, rapidly rehydrated with Phosphate-buffered saline (PBS), following which, the staining was performed.

Cytokine Array.

The level of cytokines in animal serum was determined using the cytokine array system (RayBiotech, Inc., Norcross, Ga.). The signal intensities of the array blots were quantified using ImageJ software (Schneider et al., 2012).

Statistical Analysis.

All experiments were repeated at least thrice with triplicates each time. The mean and the standard error of the mean were calculated. The data were analyzed with the Student's t test or by two way analysis of variance (ANOVA) when comparing means of more than two groups.

Example 2: 3-BrPA Deactivates the Phenotype of Activated LX-2 Cells

Figure 2:
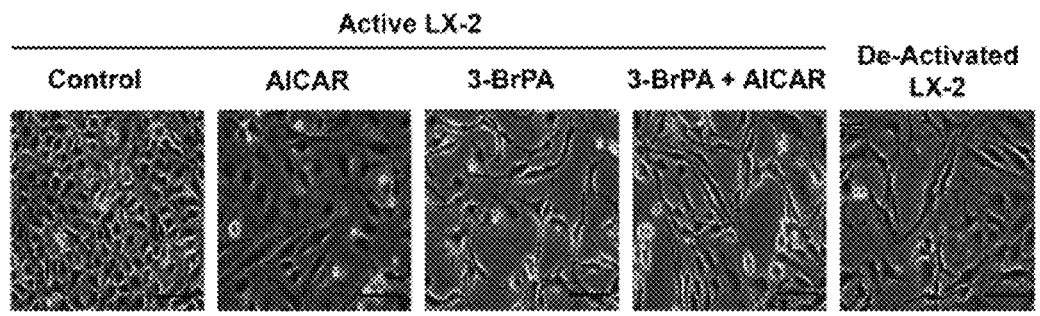
FIG. 2 contains three panels, (A)-(D), depicting 3-BrPA treatment alters the phenotype of activated LX-2 cells. Panel (A) depicts morphology of aLX-2 cells upon treatment with AICAR, 3-BrPA (25 µM), a combination of both, and deactivated LX-2 cells. Panel (B) depicts LX-2 cells treated with 3-BrPA, and 6 days post-treatment. Scale=0.5 mm. Panel (C) shows human hepatocytes on treatment with 3-BrPA. Scale=100 μm. Panel (D) shows cell viability assay showing that human hepatocytes remained unaffected by 3-BrPA (25 μM) treatment.
Figure 2:
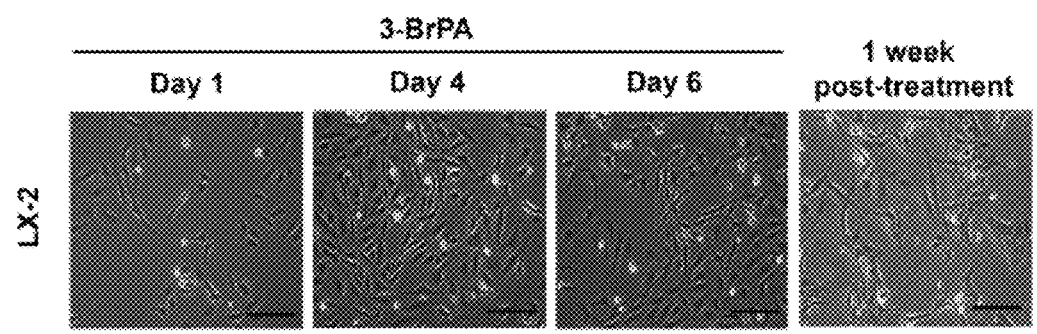
Figure 2:
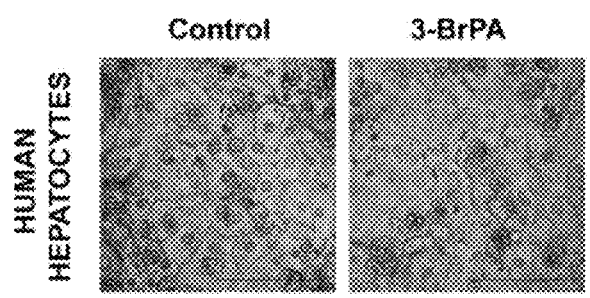
Figure 2:
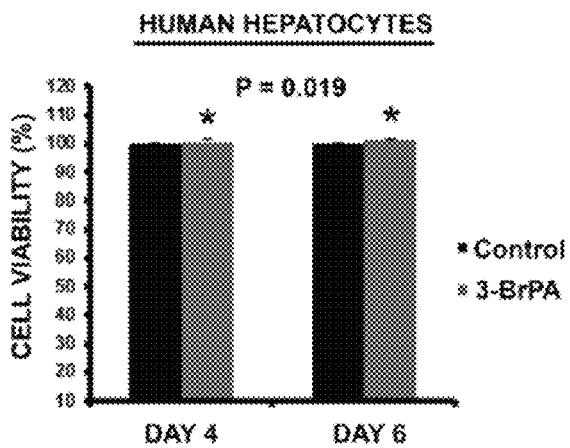

De-activated LX-2 cells were prepared as described in the methods. The morphology, proliferation and mRNA expression of markers of invasiveness and motility were evaluated in deactivated LX-2 and activated LX-2 cells (FIG. 1, Panels A-C). Activated LX-2 cells (aLX-2) have a rounded shape, lacking the stellate-like features of the de-activated cells. They also have increased proliferation, and increased expression of TGLN, Vim, SNL1, and CDH12 mRNA. The MTD of 3-BrPA in aLX-2 cells was determined to be 25 µM. Deactivated cells were compared to 3-BrPA treated aLX-2 cells. 3-BrPA treatment of aLX-2 cells induced changes in phenotype including an elongated, spindle-shaped morphology which resembled the normal, de-activated LX-2 cells (FIG. 2, Panel A). To determine if the phenotypic alterations of the aLX-2 cells are dependent on cellular stress, the cells were treated with an energy stress inducer, AICAR (Danovi, 2011), which is known to increase cellular ROS levels. Surprisingly, AICAR did not induce any change in morphology (FIG. 2, Panel A), whereas 3-BrPA promoted the changes even in the presence of AICAR. These findings indicate that 3-BrPA-dependent phenotypic alteration is independent of AICAR's action (FIG. 2, Panel A). The phenotypic changes in aLX-2 cells treated with 3-BrPA were stable, even after withdrawal of the drug (FIG. 2, Panel B). It was then investigated whether the effect of 3-BrPA is specific to aLX-2 cells, as nonspecific targeting may cause unwanted toxicity to hepatocytes. Remarkably, human primary hepatocytes did not under go any morphological change and were not sensitive to treatment with 3-BrPA at the same metronomic dose (FIG. 2, Panels C,D). Thus, a metronomic treatment with low dose 3-BrPA selectively promotes alterations in activated-LX-2 cells that alters the phenotype to resemble a de-activated LX-2 cell. Primary hepatocytes were not affected by the 3-BrPA.

Figure 3:
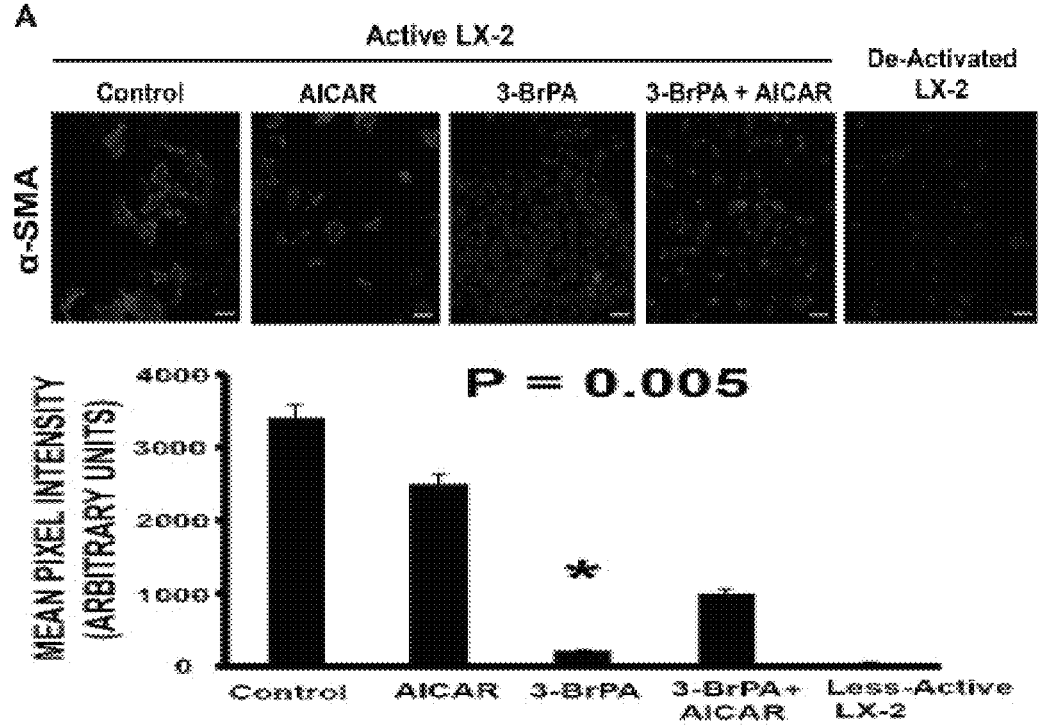
FIG. 3 contains eight panels, (A)-(H), depicting 3-BrPA treatment affects the profibogenic capacity of activated LX-2 cells. Panel (A) depicts immunofluorescent images of α-SMA. Bar graph represents the quantification of mean fluorescent intensity from at least triplicate experiments. Scale=20 μm. Panel (B) depicts immunoblot of α-SMA protein. Panel (C) shows zymogram and corresponding immunoblots of MMP-2 and MMP-9. Panel (D) shows trichrome staining of collagen. Insert shows a higher magnification of a region of interest. Scale=0.5 mm, insert=2.5 mm. Panel (E) depicts the level of $\alpha_1$ (I) collagen mRNA. Panel (F) depicts immunofluorescent images of cytokeratin (CK)-18 Scale=20 μm. Panel G shows rat aHSCs are sensitive to 3-BrPA treatment in confocal microscopic images showing a decrease in α-SMA in rat hepatic stellate cells on treatment with 3-BrPA. Scale=20 μm. Panel H shows rat aHSCs are sensitive to 3-BrPA treatment in an immunoblot showing an increase in the secretion of MMP-9 in rat hepatic stellate cells treated with 3-BrPA FIG. 4 contains five panels, (A)-(E), depicting 3-BrPA treatment deregulates energy metabolism and facilitates glycolysis in activated LX-2 cells. Immunofluorescent images showing (Panel (A)) MCT-1 to facilitate cellular uptake of 3-BrPA in LX-2 cells, (Panel (B)) a decrease in the expression level of F1-F0 ATPase (ATPSE) and (Panel (C)) an increase in the expression of MCT-4 (lactate transporter) in 3-BrPA treated LX-2 cells. Scale: left=20 μm; right=40 μm. Panel (D) depicts immunoblot showing 3-BrPA—dependent changes in the level of protein expression and numerical data represent the densitometric quantification of corresponding signals. Panel (E) depicts lactate secretion in LX-2 cells. MCT-1; monocarboxylate transporter (MCT) 1, ATPSE; Adenine tri phosphatase 5E, LDH-A; lactate dehydrogenase A.
Figure 3:
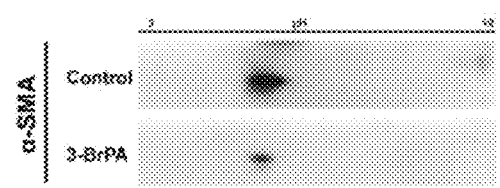
Figure 3:
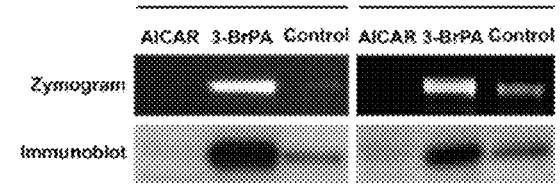
Figure 3:
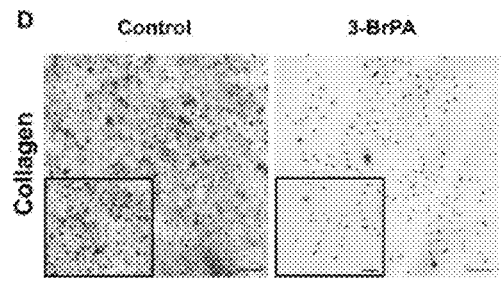
Figure 3:
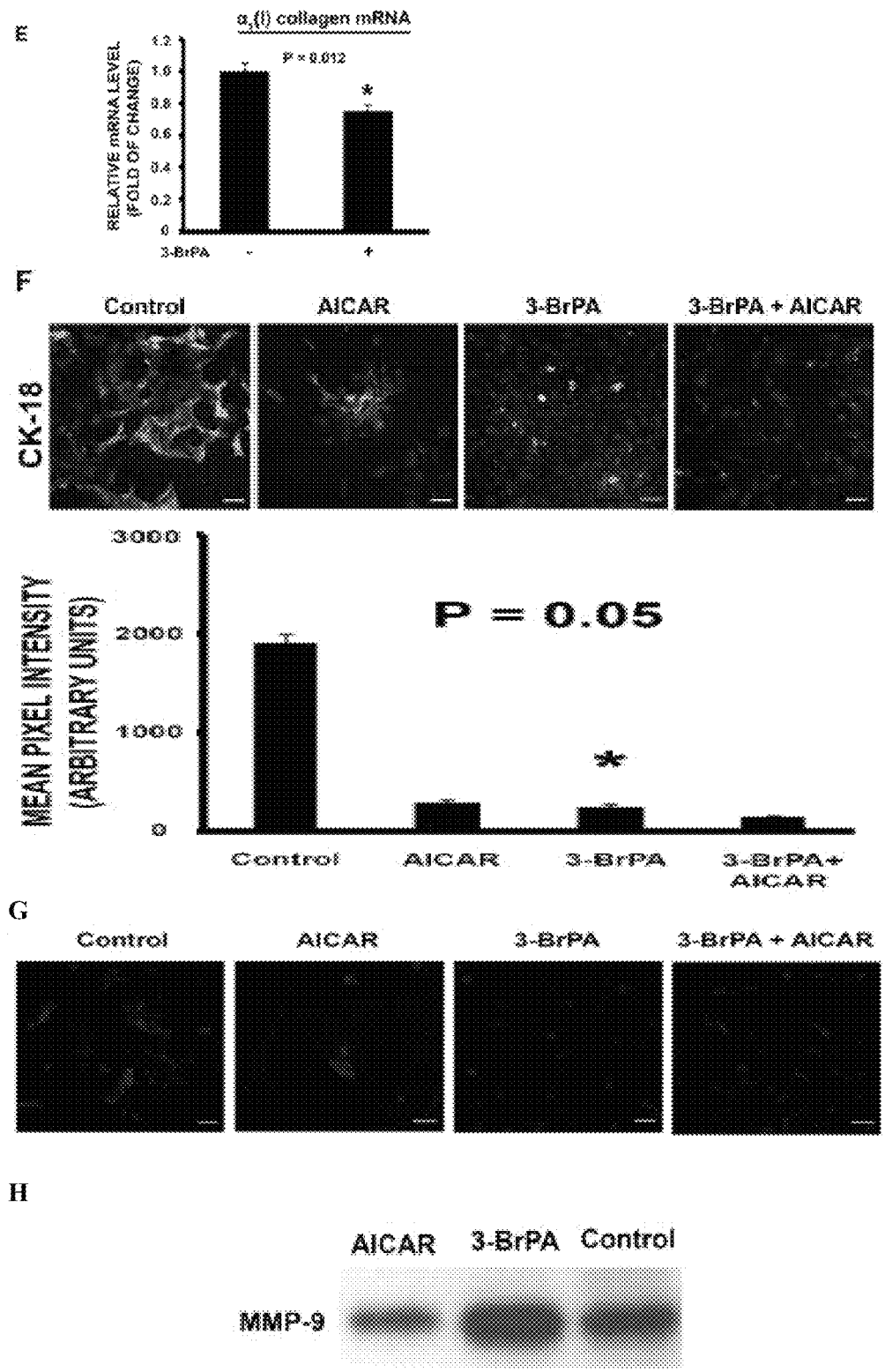

Example 3: 3-BrPA-Treatment Affects the Profibrogenic Capacity of Activated-LX-2 Cells Activated-LX-2 cells exhibit a high level of α-SMA and CK-18 expression, collagen secretion, and reduced level of extracellular MMPs, representing the typical profibrogenic phenotype. 3-BrPA treatment reduced the level of α-SMA in aLX-2 cells (FIG. 3, Panels A,B) and elevated the secretion of MMPs (FIG. 3, Panel C). 3-BrPA decreased liver collagen and α1 (I) collagen mRNA (FIG. Panels 3D,E). A prominent decrease in the level of CK-18 was also observed in 3-BrPA treated aLX-2 cells (FIG. 3, Panel F). Some of these findings were also verified in rat HSCs (FIG. 3, Panels G and H). Thus, 3-BrPA treatment reversed the biochemical (α-SMA, extracellular MMP activity, CK-18) and functional markers (secretion of MMPs and collagen) of profibrogenic, activated-LX-2 cells to resemble de-activated HSCs.

Figure 4:
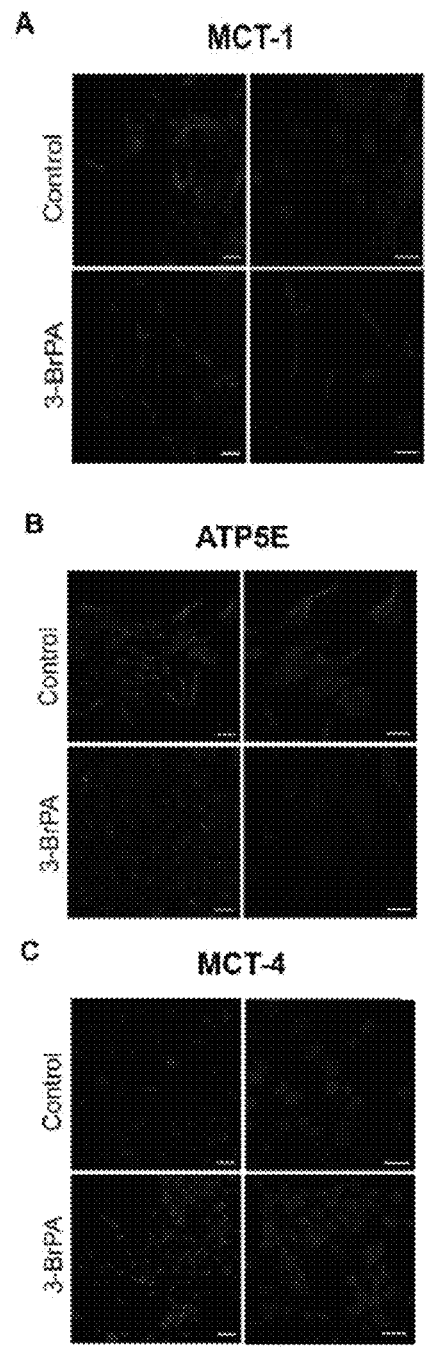
Figure 4:
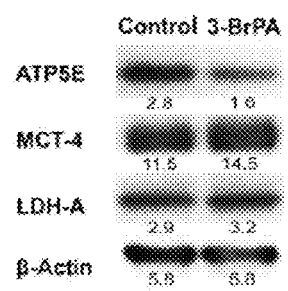
Figure 4:
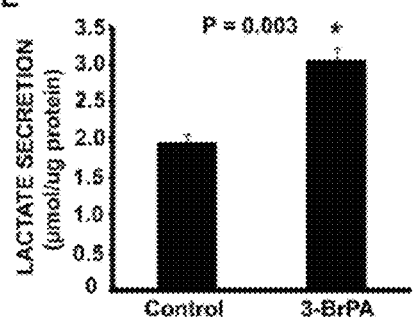

Example 4: 3-BrPA Treatment Deregulates Energy Metabolism in Activated-LX-2 Cells Cellular uptake of 3-BrPA is dependent on expression of MCT-1. The data shows that activated LX-2 cells express MCT-1 and this is unaffected by 3-BrPA treatment (FIG. 4, Panel A). 3-BrPA treatment significantly downregulated the expression of mitochondrial-membrane bound enzyme, ATPSE (also known as $F_1$-$F_0$ ATPase) (FIG. 4, Panels B,D) indicating a decrease in mitochondrial function. Notably, the expression levels of the lactate transporter, MCT-4 (FIG. 4, Panels C,D) and the enzyme lactate dehydrogenase (LDH) were increased (FIG. 4, Panel D). In corroboration, 3-BrPA treatment also increased the level of lactate secretion (FIG. 4, Panel E) indicating a metabolic reprogramming towards an increased rate of glycolysis.

Figure 5:
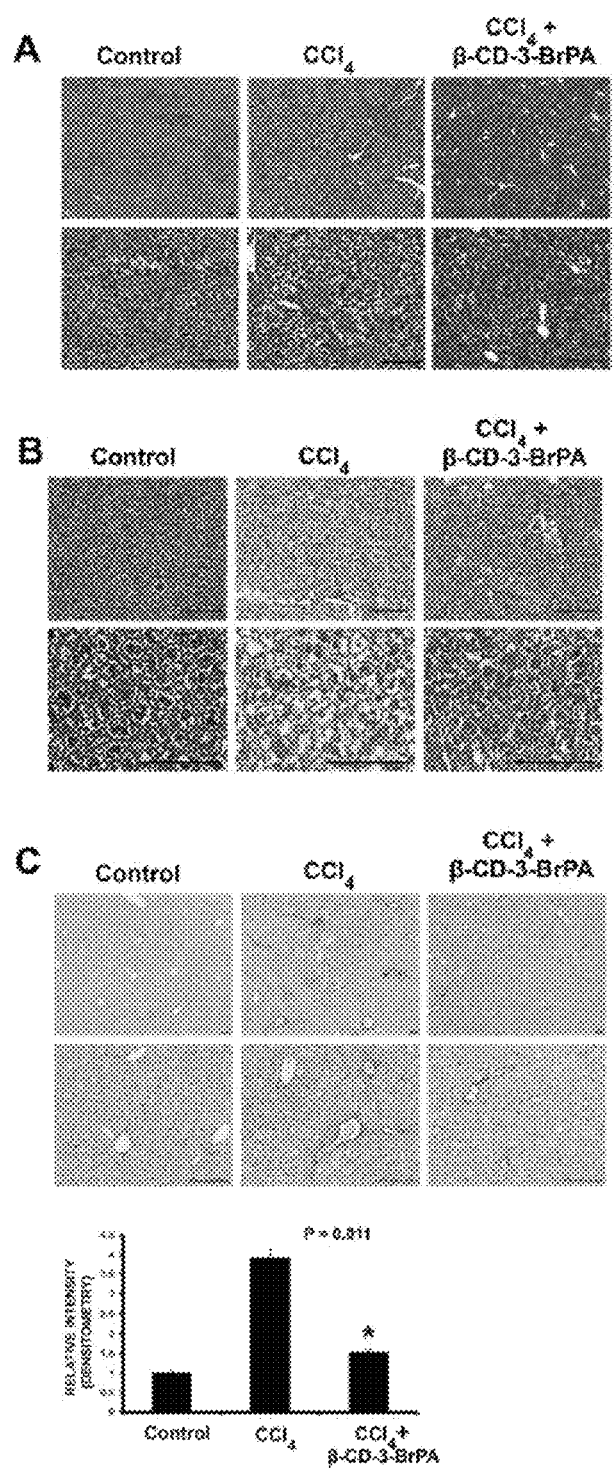
FIG. 5 contains seven panels, (A)-(G), depicting β-CD-3-BrPA treatment blocks the progression of fibrosis in vivo. Panel (A) depicts H & E staining showing changes in liver pathology in CCl$_4$ and β-CD-3-BrPA-treated mice. Scale: top panel=20 μm, bottom panel=100 μm. Liver sections stained with (Panel (B)) Trichrome and (Panel (C)) Sirius red. Scale: For (B) top panel=200 μm, bottom panel=100 μm and for (C) top panel=20 μm, bottom panel=100 μm. The level of fibrosis was measured by Sirius red staining and densitometry of various groups. The density of fibrosis was determined as intensity of Sirius red staining, divided by the area of the captured field. Total of 30 fields were captured from livers of each group of mice. The values are expressed as means±S.E. Panel (D) depicts representative confocal microscopic images showing the level of α-SMA expression with quantitative analysis of the fluorescent intensities from triplicates. Scale=20 μm. Panel (E) depicts immunoblot showing levels of leptin, ATPSE and MCT-4. β-CD-3-BrPA treatment blocks the progression of liver fibrosis. Representative images of livers from mouse subjected to CCl4-dependent induction of fibrosis either (Panel (F)) untreated (control) or (Panel (G)) treated with β-CD-3-BrPA.
Figure 5:
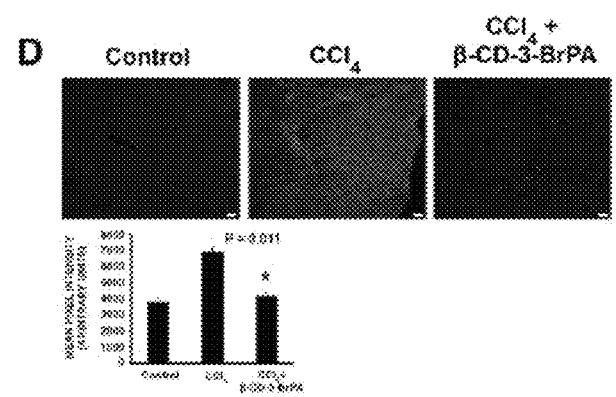
Figure 5:
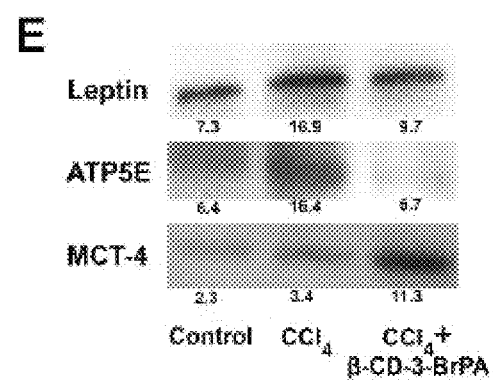
Figure 5:
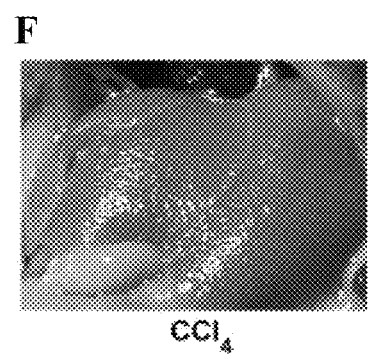
Figure 5:
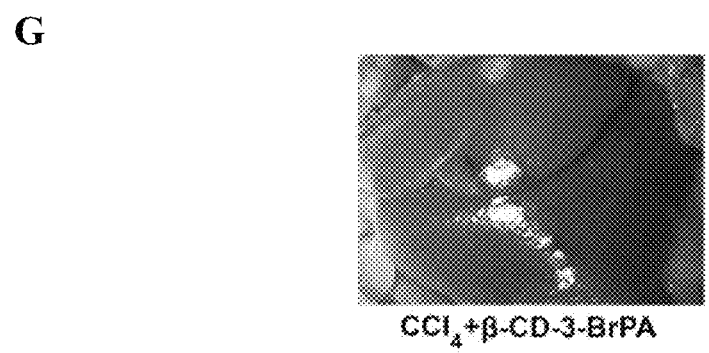

Example 5: Microencapsulated 3-BrPA Blocked the Progression of Liver Fibrosis In Vivo In vivo validation of the antifibrotic effects of 3-BrPA was performed in $CCl_4$-induced liver fibrosis in BALB/c6 black mice. As mentioned elsewhere, due to the short half-life of 3-BrPA, for the in vivo experiments we used our recently developed microencapsulated 3-BrPA using β-cyclodextrin (β-CD) (15). β-CD-3-BrPA treatment decreased hepatocyte ballooning degeneration, necrosis (FIG. 5, Panel A) and fibrosis induced by $CCl_4$ (FIG. 5, Panels B,C; F, G). The fibrotic markers α-SMA and leptin decreased in β-CD-3-BrPA treated animals (FIG. 5, Panels D,E). Immunoblot analysis of liver tissue from the control and treated animals showed a 3-CD-3-BrPA-dependent elevation in the level of MCT-4 with a concomitant reduction in mitochondrial-membrane bound enzyme, ATPSE (FIG. 5, Panel E). The results indicate that the antifibrotic effects of 3-BrPA involves deregulation of energy metabolism in this mouse model of liver fibrosis. (FIG. 5, Panel E).

Figure 6:
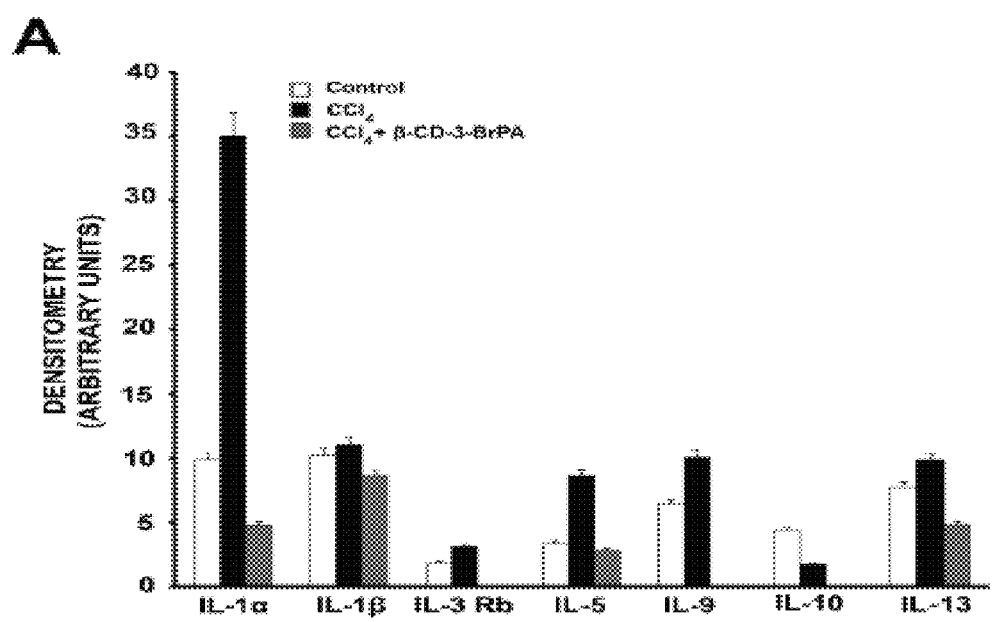
FIG. 6 contains thirteen panels, (A)-(M) depicting the effects of β-CD-3-BrPA on serum cytokines in CCl$_4$ treated mice. Panel (A) depicts interleukins. Panels (B)-(M) shows enhancers of HSC-activation and fibrotic markers. IL-3 Rb, IL-3 Receptor beta; leptin (Panel (B)); CTACK, Cutaneous T cell-attracting chemokine (Panel (C)); Eotaxin 2 (Panel (D)); G-CSF, Granulocyte colony-stimulating factor (Panel (E)); IGBP-3, Insulin-like growth factor-binding protein 3 (Panel (F)); M-CSF, Macrophage colony-stimulating factor (Panel (G)); TNF-α, Tumor necrosis factor α (Panel (H)); VEGF, Vascular endothelial growth factor (Panel (I)); CD40L Receptor (Panel (J)); CXCL, Chemokine (C-X-C motif) ligand 1 (Panel (M)); CXCL16 (Panel (K)); and CRG-2, cytokine responsive gene-2 (Panel (L)).
Figure 6:
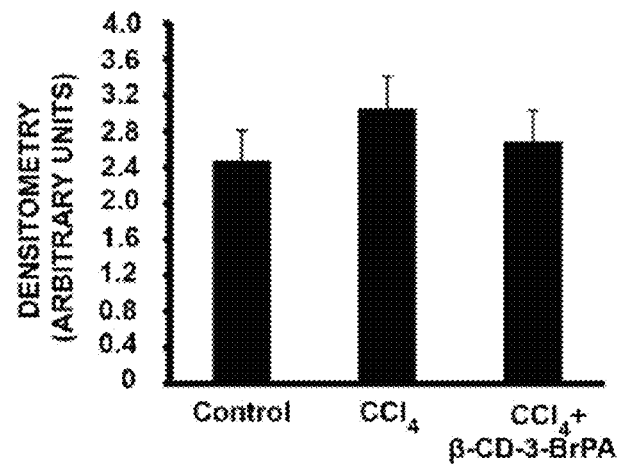
Figure 6:
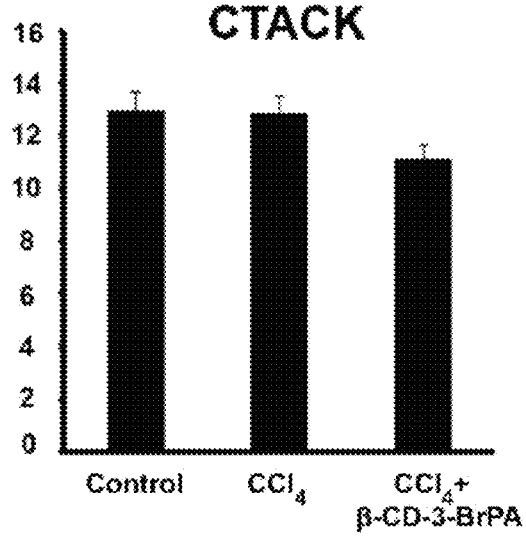
Figure 6:
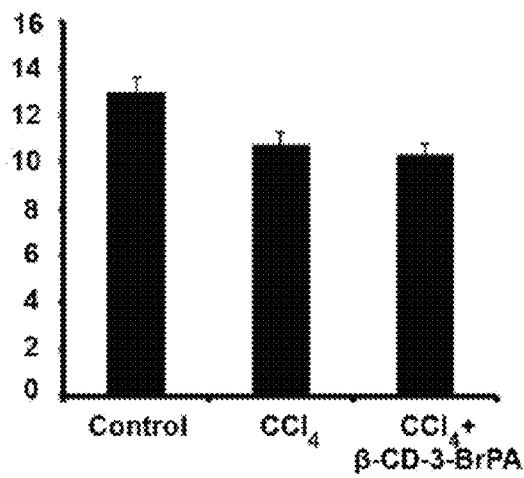
Figure 6:
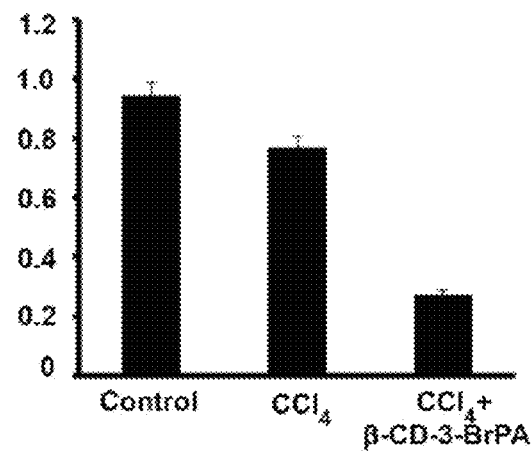
Figure 6:
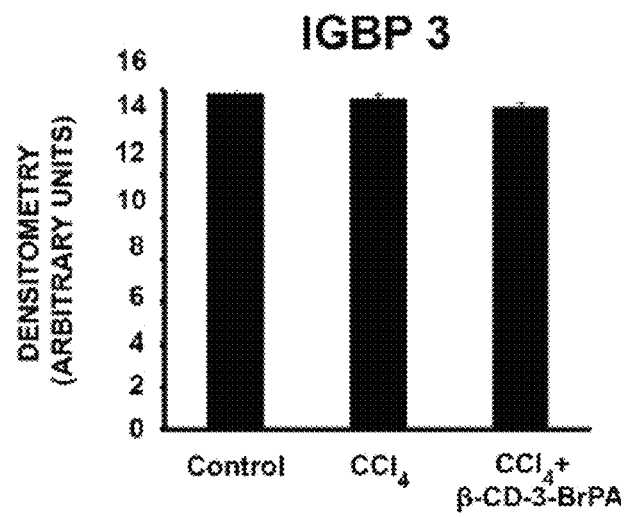
Figure 6:
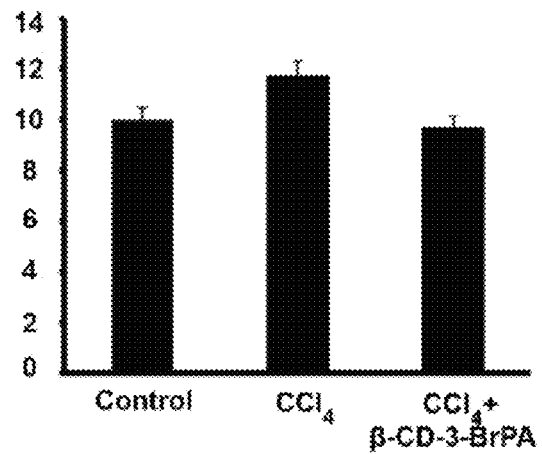
Figure 6:
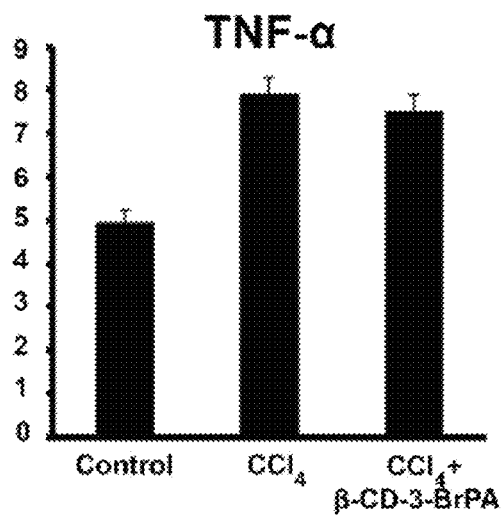
Figure 6:
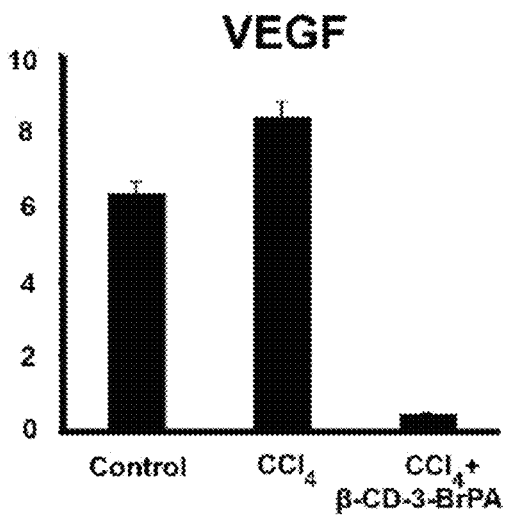
Figure 6:
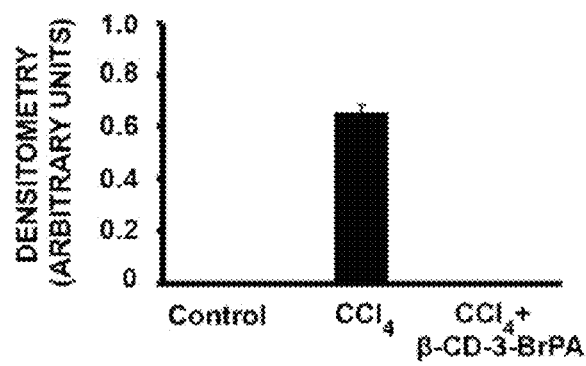
Figure 6:
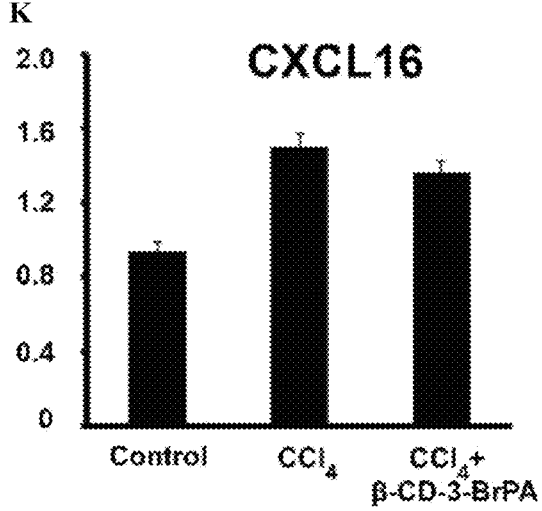
Figure 6:
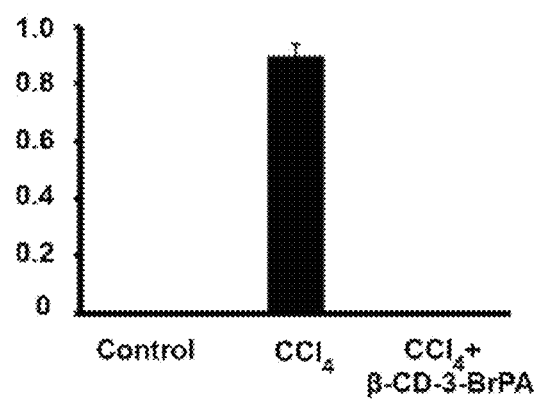
Figure 6:
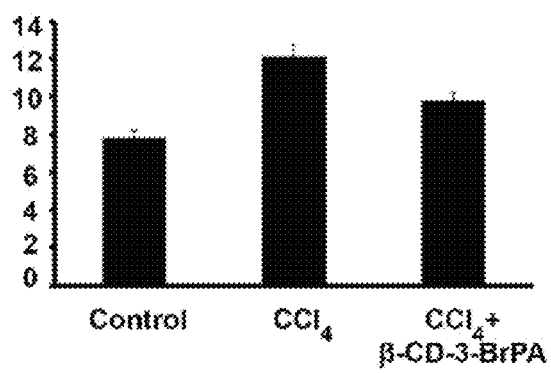

Example 6: Microencapsulated 3-BrPA Down Regulated the Secretion of Pro-Fibrotic Cytokines In Vivo Next, we investigated the effect of β-CD-3-BrPA in $CCl_4$ induced fibrosis on serum cytokines associated with inflammation and fibrosis. Compared to $CCl_4$ treatment alone, β-CD-3-BrPA reduced serum levels of pro-fibrotic interleukins IL-1, IL-3, IL-5, IL-9, IL-10 and IL-13 (FIG. 6, Panel A). β-CD-3-BrPA treatment also decreased the levels of enhancers of HSC-activation such as CD40 antigen and IGBP-3 (FIG. 6, Panels F and J). Furthermore, the antifibrotic effects of 3-BrPA was also supported by a substantial decreases in pro-fibrotic cytokines including CRG-2, CTACK, leptin, VEGF, CXCL 16, CXCL1, TNF-α and eotaxin-2. These results indicate the transition of the aHSCs towards a de-activated state. (FIG. 6, Panels B-M).

Example 6: Summary

The present study demonstrated that sublethal, low dose of 3-BrPA effectively reversed the profibrogenic phenotype of HSCs in vitro, and blocked the progression of liver fibrosis in vivo. Notably, it was demonstrated that the principle mechanism underlying the 3-BrPA-mediated phenotypic alteration and abrogation of fibrotic processes involved deregulation of energy metabolism. This is well supported by the data showing a decrease in the level of mitochondrial ATPSE with a corresponding increase in the level of the glycolytic enzyme LDH-A, the lactate transporter MCT-4 and increased cellular lactate secretion. The indicated dose 3-BrPA was not toxic to human primary hepatocytes (in vitro) and mouse hepatocytes (in vitro and in vivo). Thus, the efficacious antifibrotic dose of 3-BrPA is also safe for normal hepatocytes. In liver fibrosis or cirrhosis, preservation or conservation of healthy hepatocytes is critical for the maintenance of functional liver (Fausto and Campbell, 2003). Collectively, the findings of the current study are congruent with a potentially effective antifibrotic agent: selective targeting of activated-HSCs, reversal of functional morphology, and lack of toxic effects on primary hepatocytes (Anders and Vielhauer, 2007).

The validation of the findings relies on several lines of experimental evidence. 3-BrPA dependent phenotypic alterations were compared with a (positive) control represented by deactivated LX-2 (generated by geltrex) that mimic normal HSCs. The 3-BrPA dependent phenotypic alteration of aLX-2 cells was substantiated by a decrease in the fibrotic markers α-SMA and CK-18, a decrease in collagen mRNA, and a corresponding increase in MMPs. Furthermore, the effect of 3-BrPA on fibrotic markers were also validated in rat HSCs. 3-BrPA mediated reversal of a LX-2 (fibrogenic) into de-activated (non-fibrogenic) phenotype was stable indicating the prevention of recurrence, a potential concern in treating fibrosis (Friedman, 2010; Schuppan and Kim, 2013). Finally, the mechanism, i.e. metabolic reprogramming towards glycolysis, was validated both in vitro and in vivo. Importantly, 3-BrPA could promote its antifibrotic effects even in the presence of a stress inducer like AICAR. Intracellular stress and its enhancers (e.g. reactive oxygen species (ROS)) play a pivotal role in the propagation of fibrosis, and its progression towards cirrhosis (Hernandez-Gea et al., 2013; Paik et al., 2014) and carcinogenesis (Han and Chen, 2013; Sosa et al., 2013). Thus an effective antifibrotic agent potentially should have the ability to promote its effects despite the presence of stress inducers. Interestingly, unlike 3-BrPA's anticancer effects which rely on the inhibition of glycolysis, its
antifibrotic effects in aHSCs primarily involve down-regulation of mitochondrial ATPSE while facilitating glycolysis. This biochemical paradox is comprehensible due to the fact that in order to achieve antiglycolytic, anticancer effects 3-BrPA is required at a significantly higher dose [8 to 10 fold in vitro (Ganapathy-Kanniappan et al., 2010) or 4-5 fold in vivo (Schaefer et al., 2012)]. Next, sensitivity of aLX-2 cells or aHSCs to 3-BrPA is possible primarily due to the presence of its transporter, MCT-1. Noteworthy, abnormal cells such as cancer cells have already been known to upregulate MCT-1 which enabled us to target them using 3-BrPA (Birsoy et al., 2013). Here for the first time we demonstrate that profibrotic or fibrotic cells also express MCT-1 providing us an opportunity to selectively target such activated-HSCs.

It has been known that fibrotic or cirrhotic cells require enormous amount of intracellular energy to meet their energy demands owing to increased synthetic and secretory activities. This in turn necessitates the prevalence of functionally efficient glycolytic and mitochondrial metabolic pathways. Chen and co (Chen et al., 2012) have demonstrated that blocking hedgehog signaling pathway that affects glycolysis resulted in the mitigation of fibrotic phenotype. Here we demonstrate that selective targeting of mitochondrial-ATPSE is sufficient to block the progression of aHSCs. In conclusion, this study shows that targeting energy metabolism of activated-HSCs impairs their functional capacity resulting in the inhibition of profibrotic phenotype.

REFERENCES

Ahmad A and Ahmad R. (2012) Understanding the mechanism of hepatic fibrosis and potential therapeutic approaches. *Saudi J Gastroenterol* 18:155-167.

Anania F A, Potter J J, Rennie-Tankersley L, Mezey E. (1996) Activation by acetaldehyde of the promoter of the mouse alpha2(I) collagen gene when transfected into rat activated stellate cells. *Arch Biochem Biophys* 331:187-193.

Anders H J and Vielhauer V. (2007) Identifying and validating novel targets with in vivo disease models: Guidelines for study design. *Drug Discov Today* 12:446-451.

Birsoy K, Wang T, Possemato R, Yilmaz O H, Koch C E, Chen W W, Hutchins A W, Gultekin Y, Peterson T R, Carette J E, Brummelkamp T R, Clish C B, Sabatini D M. (2013) MCT1-mediated transport of a toxic molecule is an effective strategy for targeting glycolytic tumors. *Nat Genet* 45:104-108.

Buijs M, Vossen J A, Geschwind J F, Ishimori T, Engles J M, Acha-Ngwodo O, Wahl R L, Vali M. (2009) Specificity of the anti-glycolytic activity of 3-bromopyruvate confirmed by FDG uptake in a rat model of breast cancer. *Invest New Drugs* 27:120-123.

Buijs M, Wijlemans J W, Kwak B K, Ota S, Geschwind J F. (2013) Antiglycolytic therapy combined with an image-guided minimally invasive delivery strategy for the treatment of breast cancer. *J Vasc Interv Radiol* 24:737-743.

Chapiro J, Sur S, Savic L J, Ganapathy-Kanniappan S, Reyes J, Duran R, Thiruganasambandam S C, Moats C R, Lin M, Luo W, Tran P T, Herman J M, Semenza G L, Ewald A J, Vogelstein B, Geschwind J F. (2014) Systemic delivery of microencapsulated 3-bromopyruvate for the therapy of pancreatic cancer. *Clin Cancer Res* 20:6406-6417.

Chen Y, Choi S S, Michelotti G A, Chan I S, Swiderska-Syn M, Karaca G F, Xie G, Moylan C A, Garibaldi F, Premont R, Suliman H B, Piantadosi C A, Diehl A M. (2012) Hedgehog controls hepatic stellate cell fate by regulating metabolism. *Gastroenterology* 143:1319-29.e1-11.

Danovi S A. (2011) Therapy: Trimming the excess. *Nat Rev Cancer* 11:231. Davidescu M, Sciaccaluga M, Macchioni L, Angelini R, Lopalco P, Rambotti M G, Roberti R, Corcelli A, Castigli E, Corazzi L. (2012) Bromopyruvate mediates autophagy and cardiolipin degradation to mono-lyso-cardiolipin in GL15 glioblastoma cells. *J Bioenerg Biomembr* 44:51-60.

El-Serag, H. B. Hepatocellular carcinoma. N. Engl. J. Med. 365, 1118-1127 (2011).

El-Serag, H. B. and Rudolph, K. L. Hepatocellular carcinoma: epidemiology and molecular carcinogenesis. Gastroenterology 132, 2557-2576 (2007).

Fausto N and Campbell J S. (2003) The role of hepatocytes and oval cells in liver regeneration and repopulation. *Mech Dev* 120:117-130.

Friedman, S. L. Liver fibrosis in 2012: Convergent pathways that cause hepatic fibrosis in NASH. Nat. Rev. Gastroenterol. Hepatol. 10, 71-72 (2013).

Friedman S L. (2010) Evolving challenges in hepatic fibrosis. *Nat Rev Gastroenterol Hepatol* 7:425-436.

Friedman S L. (2008) Hepatic stellate cells: Protean, multifunctional, and enigmatic cells of the liver. *Physiol Rev* 88:125-172.

Gaca M D, Zhou X, Issa R, Kiriella K, Iredale J P, Benyon R C. (2003) Basement membrane-like matrix inhibits proliferation and collagen synthesis by activated rat hepatic stellate cells: Evidence for matrix-dependent deactivation of stellate cells. *Matrix Biol* 22:229-239.

Ganapathy-Kanniappan S, Geschwind J F, Kunjithapatham R, Buijs M, Syed L H, Rao P P, Ota S, Kwak B K, Loffroy R, Vali M. (2010) 3-bromopyruvate induces endoplasmic reticulum stress, overcomes autophagy and causes apoptosis in human HCC cell lines. *Anticancer Res* 30:923-935.

Ganapathy-Kanniappan S, Geschwind J-, Kunjithapatham R, Buijs M, Vossen J. A, Tchernyshyov I, Torbenson M. S, Cole R. N, Syed L. H, Vali M. (2009a) A pyruvic acid analog primarily targets GAPDH to promote cancer cell death. *FASEB J* 23:678.2.

Ganapathy-Kanniappan S, Geschwind J F, Kunjithapatham R, Buijs M, Vossen J A, Tchernyshyov I, Cole R N, Syed L H, Rao P P, Ota S, Vali M. (2009b) Glyceraldehyde-3-phosphate dehydrogenase (GAPDH) is pyruvylated during 3-bromopyruvate mediated cancer cell death. *Anticancer Res* 29:4909-4918.

Ganapathy-Kanniappan S, Karthikeyan S, Geschwind J F, Mezey E. (2014) Is the pathway of energy metabolism modified in advanced cirrhosis? *J Hepatol* 61:452.

Ganapathy-Kanniappan S, Kunjithapatham R, Torbenson M S, Rao P P, Carson K A, Buijs M, Vali M, Geschwind J F. (2012) Human hepatocellular carcinoma in a mouse model: Assessment of tumor response to percutaneous ablation by using glyceraldehyde-3-phosphate dehydrogenase antagonists. *Radiology* 262:834-845.

Geschwind J F, Ko Y H, Torbenson M S, Magee C, Pedersen P L. (2002) Novel therapy for liver cancer: Direct intraarterial injection of a potent inhibitor of ATP production. *Cancer Res* 62:3909-3913.

Gines P, Fernandez J, Durand F, Saliba F. (2012) Management of critically-ill cirrhotic patients. *J Hepatol* 56 Suppl 1:S13-24.

Han Y and Chen J Z. (2013) Oxidative stress induces mitochondrial DNA damage and cytotoxicity through independent mechanisms in human cancer cells. *Biomed Res Int* 2013:825065.

Hernandez-Gea V, Hilscher M, Rozenfeld R, Lim M P, Nieto N, Werner S, Devi L A, Friedman S L. (2013) Endoplasmic reticulum stress induces fibrogenic activity in hepatic stellate cells through autophagy. *J Hepatol* 59:98-104.

Hong, K., Georgiades, C. S. and Geschwind, J. F. H. Technology Insight: image-guided therapies for hepatocellular carcinoma—intra-arterial and ablative techniques. Nature Clinical Practice Oncology 3, 315-324 (2006).

Ihrlund L S, Hernlund E, Khan O, Shoshan M C. (2008) 3-bromopyruvate as inhibitor of tumour cell energy metabolism and chemopotentiator of platinum drugs. *Mol Oncol* 2:94-101.

Iredale J P, Thompson A, Henderson N C. (2013) Extracellular matrix degradation in liver fibrosis: Biochemistry and regulation. *Biochim Biophys Acta* 1832:876-883.

Jemal, A. et al. Global cancer statistics. C A Cancer. J. Clin. 61, 69-90 (2011).

Kunjithapatham R, Karthikeyan S, Geschwind J F, Kieserman E, Lin M, Fu D X, Ganapathy-Kanniappan S. (2014) Reversal of anchorage-independent multicellular spheroid into a monolayer mimics a metastatic model. *Sci Rep* 4:6816.

Lencioni, R. Loco-regional treatment of hepatocellular carcinoma. Hepatology 52, 762-773 (2010).

Liapi, E. and Geschwind, J. F. Intra-arterial therapies for hepatocellular carcinoma: where do we stand? Ann. Surg. Oncol. 17, 1234-1246 (2010).

Liapi, E. and Geschwind, J. F. Interventional oncology: new options for interstitial treatments and intravascular approaches: targeting tumor metabolism via a loco-regional approach: a new therapy against liver cancer. *J. Hepatobiliary Pancreat. Sci.* 17, 405-406 (2010).

Lim J Y, Oh M A, Kim W H, Sohn H Y, Park S I. (2012) AMP-activated protein kinase inhibits TGF-beta-induced fibrogenic responses of hepatic stellate cells by targeting transcriptional coactivator p300. *J Cell Physiol* 227:1081-1089.

Liu, X., Xu, J., Brenner, D. A. and Kisseleva, T. Reversibility of Liver Fibrosis and Inactivation of Fibrogenic Myofibroblasts. Curr. Pathobiol. Rep. 1, 209-214 (2013).

Liu, Y. et al. Inhibition of PDGF, TGF-beta, and Abl signaling and reduction of liver fibrosis by the small molecule Bcr-Abl tyrosine kinase antagonist Nilotinib. J. Hepatol. 55, 612-625 (2011).

Llovet, J. M. and Bruix, J. Novel advancements in the management of hepatocellular carcinoma in 2008. J. Hepatol. 48 Suppl 1, S20-37 (2008).

Macaron C, Hanouneh I A, Zein N N. (2010) Incidence and risk factors of hepatocellular carcinoma in patients with primary biliary cirrhosis. *Hepatology* 52:2239; author reply 2239-40.

Mallat, A. and Lotersztajn, S. Cellular Mechanisms of Tissue Fibrosis. 5. Novel insights into liver fibrosis. Am. J. Physiol. Cell. Physiol. (2013).

Nishikawa T, Bellance N, Damm A, Bing H, Zhu Z, Handa K, Yovchev M I, Sehgal V, Moss T J, Oertel M, Ram P T, Pipinos I I, Soto-Gutierrez A, Fox I J, Nagrath D. (2014) A switch in the source of ATP production and a loss in capacity to perform glycolysis are hallmarks of hepatocyte failure in advance liver disease. *J Hepatol* 60:1203-1211.

Ogawa, S. et al. Anti-PDGF-B monoclonal antibody reduces liver fibrosis development. Hepatol. Res. 40, 1128-1141 (2010).

Okuda H. (2007) Hepatocellular carcinoma development in cirrhosis. *Best Pract Res Clin Gastroenterol* 21:161-173.

Ota S, Geschwind J F, Buijs M, Wijlemans J W, Kwak B K, Ganapathy-Kanniappan S. (2013) Ultrasound-guided direct delivery of 3-bromopyruvate blocks tumor progression in an orthotopic mouse model of human pancreatic cancer. *Target Oncol* 8:145-151.

Paik Y H, Kim J, Aoyama T, De Minicis S, Bataller R, Brenner D A. (2014) Role of NADPH oxidases in liver fibrosis. *Antioxid Redox Signal* 20:2854-2872.

Pinzani M, Rosselli M, Zuckermann M. (2011) Liver cirrhosis. *Best Pract Res Clin Gastroenterol* 25:281-290.

Rodrigues-Ferreira C, da Silva A P, Galina A. (2012) Effect of the antitumoral alkylating agent 3-bromopyruvate on mitochondrial respiration: Role of mitochondrially bound hexokinase. *J Bioenerg Biomembr* 44:39-49.

Sanchez-Arago M and Cuezva J M. (2011) The bioenergetic signature of isogenic colon cancer cells predicts the cell death response to treatment with 3-bromopyruvate, iodoacetate or 5-fluorouracil. *J Transl Med* 9:19.

Sanchez-Valle, V., Chavez-Tapia, N. C., Uribe, M. and Mendez-Sanchez, N. Role of oxidative stress and molecular changes in liver fibrosis: a review. Curr. Med. Chem. 19, 4850-4860 (2012).

Schaefer N G, Geschwind J F, Engles J, Buchanan J W, Wahl R L. (2012) Systemic administration of 3-bromopyruvate in treating disseminated aggressive lymphoma. *Transl Res* 159:51-57.

Schneider C A, Rasband W S, Eliceiri K W. (2012) NIH image to ImageJ: 25 years of image analysis. *Nat Methods* 9:671-675.

Schuppan D and Kim Y O. (2013) Evolving therapies for liver fibrosis. *J Clin Invest* 123:1887-1901.

Sohara N, Znoyko I, Levy M T, Trojanowska M, Reuben A. (2002) Reversal of activation of human myofibroblast-like cells by culture on a basement membrane-like substrate. *J Hepatol* 37:214-221.

Sosa V, Moline T, Somoza R, Paciucci R, Kondoh H, LLeonart M E. (2013) Oxidative stress and cancer: An overview. *Ageing Res Rev* 12:376-390.

Tang M, Potter J J, Mezey E. (2003) Activation of the human alpha1 (I) collagen promoter by leptin is not mediated by transforming growth factor beta responsive elements. *Biochem Biophys Res Commun* 312:629-633.

Troeger J S, Mederacke I, Gwak G Y, Dapito D H, Mu X, Hsu C C, Pradere J P, Friedman R A, Schwabe R F. (2012) Deactivation of hepatic stellate cells during liver fibrosis resolution in mice. *Gastroenterology* 143:1073-83.e22.

Wang L, Potter J J, Rennie-Tankersley L, Novitskiy G, Sipes J, Mezey E. (2007) Effects of retinoic acid on the development of liver fibrosis produced by carbon tetrachloride in mice. *Biochim Biophys Acta* 1772:66-71.

Wells R G. (2008) Cellular sources of extracellular matrix in hepatic fibrosis. *Clin Liver Dis* 12:759-68, viii.

Wu J and Zern M A. (2000) Hepatic stellate cells: A target for the treatment of liver fibrosis. *J Gastroenterol* 35:665-672.

INCORPORATION BY REFERENCE

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

EQUIVALENTS

Although the foregoing subject matter has been described in some detail by way of illustration and example for purposes of clarity of understanding, it will be understood by those skilled in the art that certain changes and modifications can be practiced within the scope of the appended claims.

---

What is claimed:

1. A method inhibiting an activated hepatic stellate cell (HSC) in an injured or inflamed liver by contacting the activated HSC with an effective amount of 3-bromopyruvate.

2. The method of claim 1, wherein said effective amount of 3-bromopyruvate is not toxic to said activated hepatic stellate cell.

3. The method of claim 1, wherein said effective amount of 3-bromopyruvate inhibits the activated hepatic stellate cell after the 3-bromopyrate molecules are no longer present in the cell.

4. The method of claim 1, performed in vitro, in vivo, or ex vivo.

* * * * *